United States Patent
Medin et al.

(10) Patent No.: US 12,076,344 B2
(45) Date of Patent: Sep. 3, 2024

(54) T-Rapa CELLS AS NOVEL EFFECTOR CELL TYPE FOR CHIMERIC ANTIGEN RECEPTOR THERAPY

(71) Applicant: The Medical College of Wisconsin, Inc., Milwaukee, WI (US)

(72) Inventors: Jeffrey A. Medin, Shorewood, WI (US); Robyn A. Oldham, Milwaukee, WI (US); Daniel H. Fowler, Bethesda, MD (US); Tania Felizardo, Charlottesville, VA (US)

(73) Assignees: The Medical College of Wisconsin, Inc., Milwaukee, WI (US); University of Virginia Patent Foundation, Charlottesville, VA (US)

( * ) Notice: Subject to any disclaimer, the term of this patent is extended or adjusted under 35 U.S.C. 154(b) by 443 days.

(21) Appl. No.: 17/296,859

(22) PCT Filed: Nov. 27, 2019

(86) PCT No.: PCT/US2019/063573
§ 371 (c)(1),
(2) Date: May 25, 2021

(87) PCT Pub. No.: WO2020/112975
PCT Pub. Date: Jun. 4, 2020

(65) Prior Publication Data
US 2022/0016167 A1    Jan. 20, 2022

Related U.S. Application Data

(60) Provisional application No. 62/773,339, filed on Nov. 30, 2018.

(51) Int. Cl.
*A61K 35/17* (2015.01)
*C12N 5/0783* (2010.01)

(52) U.S. Cl.
CPC ............ *A61K 35/17* (2013.01); *C12N 5/0636* (2013.01); *C12N 2501/04* (2013.01); *C12N 2501/2302* (2013.01); *C12N 2501/24* (2013.01); *C12N 2510/00* (2013.01)

(58) Field of Classification Search
None
See application file for complete search history.

(56) References Cited

U.S. PATENT DOCUMENTS

2017/0218337 A1 * 8/2017 Friedman ................ A61P 25/00

OTHER PUBLICATIONS

Katarzyna Szymańska and Sophie Park. Non-Hodgkin Lymphoma: Diagnosis and Treatment. Encyclopedia of Cancer (Third Edition). 2019, pp. 44-47.https://doi.org/10.1016/B978-0-12-801238-3.65271-6. Epub Nov. 5, 2018. (Year: 2018).*

Dana-Farber Cancer Institute. (2023). How car T-cell therapy works. Accessed Dec. 18, 2023. https://www.dana-farber.org/cancer-care/treatment/cellular-therapies/car-t-cell-therapy/how-car-t-cell-therapy-works#:~:text=Infusion%3A%20When%20the%20CAR%20T,of%20the%20newly%2Dengineered%20cells. (Year: 2023).*

Altogen Labs. (2023). Raji Xenograft Model. Accessed Dec. 18, 2023. https://altogenlabs.com/xenograft-models/lymphoma-xenograft/raji-xenograft-model/ (Year: 2023).*

Carlo, M.I. et. al., "A Phase Ib Study of BEZ235, a Dual Inhibitor of Phosphatidylinositol 3-Kinase (PI3K) and Mammalian Target of Rapamycin (mTOR), in Patients with Advanced Renal Cell Carcinoma", The Oncologist, 2016; 21:787-788d.

Ghione, S. et al., "Protein Kinase Inhibitor-Mediated Immunophrophylatic and Immunotherapeutic Control of Colon Cancer", Frontiers in Immunology, Apr. 2022, vol. 13, Article 875764, pp. 1-13.

Pollzzi, K.N. et al., "Regulation of T cells by mTOR: The known knowns and the known unknowns", Trends Immunol., Jan. 2015; 36(1): 13-20.

Leung, W. et al., "Sensitive and adaptable pharmacological control of CAR T cells through extracellular receptor dimerization", JCI Insight, Jun. 6, 2019; 4(11): e124430; p. 1-18.

Oldham, R.A.A. et al., "CAR-Modified Th1/Tc1-Polarized T-Rapa Cells Dissociate Inflammatory Cytokine Secretion from Anti-Tumor Cytotoxicity", Blood (2018) 132 (Supplement 1): 2046, Abstract.

Grupp, S.A. et al., "Chimeric Antigen Receptor-Modified T Cells for Acute Lymphoid Leukemia", N Engl J Med. Apr. 18, 2013; 368(16): 1509-1518.

Jung, Ji Won et al., "Tear Cytokines as Biomarkers for Chronic Graft-versus-Host Disease", Biol. Blood Marrow Transplant 21 (2015) 2079-2085.

Maude, S.L. et al., "Tisagenlecleucel in Children and Young Adults with B-Cell Lymphoblastic Leukemia", N Engl J Med., Feb. 1, 2018; 378(5); 439-448.

Foley, J.E. et al., "Ex Vivo Rapamycin Generates Donor Th2 Cells That Potently Inhibit Graft-versus-Host Disease and Graft-versus-Tumor Effects via an IL-4-Dependent Mechanism", The Journal of Immunology, (2005) 175(9): 5732-5743.

Fowler, D.H. et al., "Phase 2 clinical trial of rapamycin-resistant donor CD4+ Th2/Th1 (T-Rapa) cells after low-intensity allogeneic hematopoietic cell transplantation", Blood, Apr. 11, 2013, vol. 121, No. 15, pp. 2864-2874.

Amarnath, S. et al., "Rapamycin generates anti-apoptotic human Th1/Tc1 cells via autophagy for induction of xenogeneic GVHD", Autophagy, May 2010; 6(4): 523-541.

Mariotti, J. et al. "Ex Vivo Rapamycin Generates Apoptosis-Resistant Donor Th2 Cells that Persist in Vivo and Prevent Hemopoietic Stem Cell Graft Rejection", J. Immunol (2008) 180 (1): 89-105.

(Continued)

*Primary Examiner* — Allison M Fox
*Assistant Examiner* — Alyssa G Weston
(74) *Attorney, Agent, or Firm* — Quarles & Brady LLP

(57) ABSTRACT

The present disclosure provides chimeric antigen receptor (CAR)-T-Rapa cells and methods of making and using them. Specifically, methods of producing T-Rapa cells that can express chimeric antigen receptors is provided.

19 Claims, 11 Drawing Sheets
Specification includes a Sequence Listing.

(56) References Cited

OTHER PUBLICATIONS

Barrett, D.M. et al., "Interleukin 6 is Not Made by Chimeric Antigen Receptor T Cells and Does Not Impact Their Function", Blood (2016) 128 (22): 654.

Jung, U.J. et al., "Ex Vivo Rapamycin Generates Th1/Tc1 or Th2/Tc2 Effector T Cells with Enhanced In Vivo Function and Differential Sensitivity to Post-Transplant Rapamycin Therapy", Biology of Blood and Marrow Transplantation, 12:905-918 (2006).

Oldham, R.A.A. et al., "Practical considerations for chimeric antigen receptor design and delivery", Expert Opinion on Biological Therapy, Jun. 2017, 18 pages, https://doi.org/10.1080/14712598.2017.1339687.

Norelli, M. et al., "Monocyte-derived IL-1 and IL-6 are differentially required for cytokine-release syndrome and neurotoxicity due to CAR T cells", Nature Medicine, vol. 24, Jun. 2018, 739-748.

\* cited by examiner

SEQUENCE LISTING

<160> NUMBER OF SEQ ID NOS: 3

<210> SEQ ID NO 1
<211> LENGTH: 1461
<212> TYPE: DNA
<213> ORGANISM: Artificial Sequence
<220> FEATURE:
<223> OTHER INFORMATION: Synthetic- CD19 CAR

<400> SEQUENCE: 1

```
atggccttac cagtgaccgc cttgctcctg ccgctggcct tgctgctcca cgccgccagg      60
ccggaggtga aactgcagga gtcaggacct ggcctggtgg cgccctcaca gagcctgtcc     120
gtcacatgca ctgtctcagg ggtctcatta cccgactatg gtgtaagctg gattcgccag     180
cctccacgaa agggtctgga gtggctggga gtaatatggg gtagtgaaac cacatactat     240
```

```
aattcagctc tcaaatccag actgaccatc atcaaggaca actccaagag ccaagttttc    300
ttaaaaatga acagtctgca aactgatgac acagccattt actactgtgc caaacattat    360
tactacggtg gtagctatgc tatggactac tggggccaag aacctcagt caccgtctcc     420
tcaggtggcg gtggctcggg cggtggtggg tcgggtggcg gcggatctga catccagatg    480
acacagacta catcctccct gtctgcctct ctgggagaca gagtcaccat cagttgcagg    540
gcaagtcagg acattagtaa atatttaaat tggtatcagc agaaaccaga tggaactgtt    600
aaactcctga tctaccatac atcaagatta cactcaggag tcccatcaag gttcagtggc    660
agtgggtctg gaacagatta ttctctcacc attagcaacc tggagcaaga agatattgcc    720
acttactttt gccaacaggg taatacgctt ccgtacacgt tcggagggggg gaccaagctg   780
gagatcacaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acttcgcctg tgatatctac atctgggcgc ccttggccgg acttgtgggg    960
gtccttctcc tgtcactggt tatcacccttt tactgcaaac ggggcagaaa gaaactcctg  1020
tatatattca acaaccatt tatgagacca gtacaaacta ctcaagagga agatggctgt    1080
agctgccgat ttccagaaga agaagaagga ggatgtgaac tgagagtgaa gttcagcagg   1140
agcgcagacg ccccccgcgta caagcagggc cagaaccagc tctataacga gctcaatcta  1200
ggacgaagag aggagtacga tgttttggac aagacgtg gccgggaccc tgagatgggg   1260
ggaaagccga aaggaagaa ccctcaggaa ggcctgtaca atgaactgca gaaagataag  1320
atggcggagg cctacagtga gattgggatg aaaggcgagc gccggagggg caaggggcac   1380
gatggccttt accagggtct cagtacagcc accaaggaca cctacgacgc ccttcacatg   1440
caggcccctgc cccctcgcta g                                            1461
```

<210> SEQ ID NO 2
<211> LENGTH: 486
<212> TYPE: PRT
<213> ORGANISM: Artificial Sequence
<220> FEATURE:
<223> OTHER INFORMATION: Synthetic- CD19 CAR

<400> SEQUENCE: 2

```
Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Gly Leu
            20                  25                  30

Val Ala Pro Ser Gln Ser Leu Ser Val Thr Cys Thr Val Ser Gly Val
        35                  40                  45

Ser Leu Pro Asp Tyr Gly Val Ser Trp Ile Arg Gln Pro Pro Arg Lys
    50                  55                  60

Gly Leu Glu Trp Leu Gly Val Ile Trp Gly Ser Glu Thr Thr Tyr Tyr
65                  70                  75                  80

Asn Ser Ala Leu Lys Ser Arg Leu Thr Ile Ile Lys Asp Asn Ser Lys
                85                  90                  95

Ser Gln Val Phe Leu Lys Met Asn Ser Leu Gln Thr Asp Asp Thr Ala
            100                 105                 110

Ile Tyr Tyr Cys Ala Lys His Tyr Tyr Tyr Gly Gly Ser Tyr Ala Met
        115                 120                 125

Asp Tyr Trp Gly Gln Gly Thr Ser Val Thr Val Ser Ser Gly Gly Gly
    130                 135                 140
```

```
Gly Ser Gly Gly Gly Ser Gly Gly Gly Ser Asp Ile Gln Met
145                 150                 155                 160

Thr Gln Thr Thr Ser Ser Leu Ser Ala Ser Leu Gly Asp Arg Val Thr
                165                 170                 175

Ile Ser Cys Arg Ala Ser Gln Asp Ile Ser Lys Tyr Leu Asn Trp Tyr
            180                 185                 190

Gln Gln Lys Pro Asp Gly Thr Val Lys Leu Leu Ile Tyr His Thr Ser
        195                 200                 205

Arg Leu His Ser Gly Val Pro Ser Arg Phe Ser Gly Ser Gly Ser Gly
    210                 215                 220

Thr Asp Tyr Ser Leu Thr Ile Ser Asn Leu Glu Gln Glu Asp Ile Ala
225                 230                 235                 240

Thr Tyr Phe Cys Gln Gln Gly Asn Thr Leu Pro Tyr Thr Phe Gly Gly
                245                 250                 255

Gly Thr Lys Leu Glu Ile Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 3
<211> LENGTH: 10272
<212> TYPE: DNA
<213> ORGANISM: Artificial Sequence
<220> FEATURE:
<223> OTHER INFORMATION: Synthetic- lentiviral vector encoding CD19 CAR
      (PDY.CD19.CAR.HL.IRES.EGFP)

<400> SEQUENCE: 3
gggcgaattg ggcccgacgt cgcatgcttg aagggctaa ttcactccca aagaagacaa        60
```

```
gatatccttg atctgtggat ctaccacaca caaggctact tccctgatta gcagaactac    120
acaccagggc cagggtcag atatccactg acctttggat ggtgctacaa gctagtacca    180
gttgagccag ataaggtaga agaggccaat aaaggagaga acaccagctt gttacaccct    240
gtgagcctgc atgggatgga tgacccgag agagaagtgt tagagtggag gtttgacagc    300
cgcctagcat ttcatcacgt ggcccgagag ctgcatccgg agtacttcaa gaactgctga    360
tatcgagctt gctacaaggg actttccgct ggggactttc cagggaggcg tggcctgggc    420
gggactgggg agtggcgagc cctcagatcc tgcatataag cagctgcttt ttgcctgtac    480
tgggtctctc tggttagacc agatctgagc ctgggagctc tctggctaac tagggaaccc    540
actgcttaag cctcaataaa gcttgccttg agtgcttcaa gtagtgtgtg cccgtctgtt    600
gtgtgactct ggtaactaga gatccctcag accctttag tcagtgtgga aaatctctag    660
cagtggcgcc cgaacaggga cttgaaagcg aaagggaaac cagaggagct ctctcgacgc    720
aggactcggc ttgctgaagc gcgcacggca agaggcgagg ggcggcgact ggtgagtacg    780
ccaaaaattt tgactagcgg aggctagaag agagagatg ggtgcgagag cgtcagtatt    840
aagcggggga gaattagatc gcgatgggaa aaaattcggt taaggccagg gggaagaaaa    900
aaatataaat taaaacatat agtatgggca agcagggagc tagaacgatt cgcagttaat    960
cctggcctgt tagaaacatc agaaggctgt agacaaatac tgggacagct acaaccatcc    1020
cttcagacag gatcagaaga acttagatca ttatataata cagtagcaac cctctattgt    1080
gtgcatcaaa ggatagagat aaaagacacc aaggaagctt tagacaagat agaggaagag    1140
caaaacaaaa gtaagaccac cgcacagcaa gcggccgctg atcttcagac ctggaggagg    1200
agatatgagg gacaattgga gaagtgaatt atataaatat aaagtagtaa aaattgaacc    1260
attaggagta gcacccacca aggcaaagag aagagtggtg cagagagaaa aaagagcagt    1320
gggaatagga gctttgttcc ttgggttctt gggagcagca ggaagcacta tgggcgcagc    1380
gtcaatgacg ctgacggtac aggccagaca attattgtct ggtatagtgc agcagcagaa    1440
caatttgctg agggctattg aggcgcaaca gcatctgttg caactcacag tctggggcat    1500
caagcagctc caggcaagaa tcctggctgt ggaaagatac ctaaaggatc aacagctcct    1560
ggggatttgg ggttgctctg gaaaactcat ttgcaccact gctgtgcctt ggaatgctag    1620
ttggagtaat aaatctctgg aacagatttg gaatcacacg acctggatgg agtgggacag    1680
agaaattaac aattacacaa gcttaataca ctccttaatt gaagaatcgc aaaaccagca    1740
agaaaagaat gaacaagaat tattggaatt agataaatgg gcaagtttgt ggaattggtt    1800
taacataaca aattggctgt ggtatataaa attattcata atgatagtag gaggcttggt    1860
aggtttaaga atagttttg ctgtactttc tatagtgaat agagttaggc agggatattc    1920
accattatcg tttcagaccc acctcccaac cccgaggga cccgacaggc ccgaaggaat    1980
agaagaagaa ggtggagaga gagacagaga cagatccatt cgattagtga acggatctcg    2040
acgggatcga ttttaaaaga aagggggga ttggggggta cagtgcaggg gaaagaatag    2100
tagacataat agcaacagac atacaaacta agaattaca aaacaaatt acaaaaattc    2160 aaaattttat cgataagctt tgcaaagatg gataagtttt aaacagaga ggaatctttg    2220 cagctaatgg accttctagg tcttgaaagg agtgggaatt ggctccggtg cccgtcagtg    2280
ggcagagcgc acatcgccca cagtcccga gaagttgggg ggagggtcg gcaattgaac    2340 cggtgcctag agaaggtggc gcggggtaaa ctggaaagt gatgtcgtgt actggctccg    2400 ccttttttccc gagggtgggg gagaaccgta tataagtgca gtagtcgccg tgaacgttct    2460
```

```
ttttcgcaac gggtttgccg ccagaacaca ggtaagtgcc gtgtgtggtt cccgcgggcc    2520
tggcctcttt acgggttatg gcccttgcgt gccttgaatt acttccacct ggctgcagta    2580
cgtgattctt gatcccgagc ttcgggttgg aagtgggtgg gagagttcga ggccttgcgc    2640
ttaaggagcc ccttcgcctc gtgcttgagt tgaggcctgg cctgggcgct ggggccgccg    2700
cgtgcgaatc tggtggcacc ttcgcgcctg tctcgctgct ttcgataagt ctctagccat    2760
ttaaaatttt tgatgacctg ctgcgacgct ttttttctgg caagatagtc ttgtaaatgc    2820
gggccaagat ctgcacactg gtatttcggt ttttggggcc gcgggcggcg acggggcccg    2880
tgcgtcccag cgcacatgtt cggcgaggcg gggcctgcga gcgcggccac cgagaatcgg    2940 acggggtag tctcaagctg gccggcctgc tctggtgcct ggcctcgcgc cgccgtgtat    3000
cgccccgccc tgggcggcaa ggctggcccg gtcggcacca gttgcgtgag cggaaagatg    3060
gccgcttccc ggccctgctg cagggagctc aaaatggagg acgcggcgct cgggagagcg    3120
ggcgggtgag tcacccacac aaaggaaaag ggcctttccg tcctcagccg tcgcttcatg    3180
tgactccacg gagtaccggg cgccgtccag gcacctcgat tagttctcga gcttttggag    3240
tacgtcgtct ttaggttggg gggagggggtt ttatgcgatg gagtttcccc acactgagtg    3300
ggtggagact gaagttaggc cagcttggca cttgatgtaa ttctccttgg aatttgccct    3360
ttttgagttt ggatcttggt tcattctcaa gcctcagaca gtggtcaaa gttttttcttct    3420 tccatttcag gtgtcgtgag gaattcccg ggaagccgcc accatggcct taccagtgac    3480
cgccttgctc ctgccgctgg ccttgctgct ccacgccgcc aggccggagg tgaaactgca    3540
ggagtcagga cctggcctgg tggcgccctc acagagcctg tccgtcacat gcactgtctc    3600 agggtctca ttacccgact atggtgtaag ctggattcgc cagcctccac gaaagggtct    3660
ggagtggctg ggagtaatat ggggtagtga aaccacatac tataattcag ctctcaaatc    3720
cagactgacc atcatcaagg acaactccaa gagccaagtt ttcttaaaaa tgaacagtct    3780
gcaaactgat gacacagcca tttactactg tgccaaacat tattactacg gtggtagcta    3840
tgctatggac tactggggcc aaggaacctc agtcaccgtc tcctcaggtg gcggtggctc    3900
gggcggtggt gggtcgggtg gcggcggatc tgacatccag atgacacaga ctacatcctc    3960
cctgtctgcc tctctgggag acagagtcac catcagttgc agggcaagtc aggacattag    4020
taaatattta aattggtatc agcagaaacc agatggaact gttaaactcc tgatctacca    4080
tacatcaaga ttacactcag gagtcccatc aaggttcagt ggcagtgggt ctggaacaga    4140
ttattctctc accattagca acctggagca agaagatatt gccacttact tttgccaaca    4200
gggtaatacg cttccgtaca cgttcggagg ggggaccaag ctggagatca acccacgac     4260 gccagcgccg cgaccaccaa caccggcgcc caccatcgcg tcgcagcccc tgtccctgcg    4320
cccagaggcg tgccggccag cggcgggggg cgcagtgcac acgagggggc tggacttcgc    4380
ctgtgatatc tacatctggg cgcccttggc cgggacttgt ggggtccttc tcctgtcact    4440
ggttatcacc ctttactgca acggggcag aaagaaactc ctgtatatat tcaaacaacc    4500
atttatgaga ccagtacaaa ctactcaaga ggaagatggc tgtagctgcc gatttccaga    4560
agaagaagaa ggaggatgtg aactgagagt gaagttcagc aggagcgcag acgcccccgc    4620
gtacaagcag ggccagaacc agctctataa cgagctcaat ctaggacgaa gagaggagta    4680
cgatgttttg gacaagagac gtggccggga ccctgagatg ggggaaagc cgagaaggaa    4740 gaaccctcag gaaggcctgt acaatgaact gcagaaagat aagatggcgg aggcctacag    4800
```

```
tgagattggg atgaaaggcg agcgccggag gggcaagggg cacgatggcc tttaccaggg    4860
tctcagtaca gccaccaagg acacctacga cgcccttcac atgcaggccc tgccccctcg    4920
ctagggatcc gccgctctcc ctcccccccc cctaacgtta ctggccgaag ccgcttggaa    4980
taaggccggt gtgcgtttgt ctatatgtta ttttccacca tattgccgtc ttttggcaat    5040
gtgagggccc ggaaacctgg ccctgtcttc ttgacgagca ttcctagggg tctttcccct    5100
ctcgccaaag gaatgcaagg tctgttgaat gtcgtgaagg aagcagttcc tctgaagct     5160
tcttgaagac aaacaacgtc tgtagcgacc ctttgcaggc agcggaaccc cccacctggc    5220
gacaggtgcc tctgcggcca aaagccacgt gtataagata cacctgcaaa ggcggcacaa    5280
ccccagtgcc acgttgtgag ttggatagtt gtggaaagag tcaaatggct ctcctcaagc    5340
gtattcaaca aggggctgaa ggatgcccag aaggtacccc attgtatggg atctgatctg    5400
gggcctcggt acacatgctt tacatgtgtt tagtcgaggt taaaaaaacg tctaggcccc    5460
ccgaaccacg gggacgtggt tttcctttga aaaacgat gatatcatat ggccacaacc       5520
atggtgagca agggcgagga gctgttcacc ggggtggtgc ccatcctggt cgagctggac    5580
ggcgacgtaa acggccacaa gttcagcgtg tccggcgagg gcgagggcga tgccacctac    5640
ggcaagctga ccctgaagtt catctgcacc accggcaagc tgcccgtgcc ctggcccacc    5700
ctcgtgacca cccctgaccta cggcgtgcag tgcttcagcc gctaccccga ccacatgaag    5760
cagcacgact cttcaagtc cgccatgccc gaaggctacg tccaggagcg caccatcttc    5820
ttcaaggacg acggcaacta caagacccgc gccgaggtga agttcgaggg cgacaccctg    5880
gtgaaccgca tcgagctgaa gggcatcgac ttcaaggagg acggcaacat cctggggcac    5940
aagctggagt acaactacaa cagccacaac gtctatatca tggccgacaa gcagaagaac    6000
ggcatcaagg tgaacttcaa gatccgccac aacatcgagg acggcagcgt gcagctcgcc    6060
gaccactacc agcagaacac ccccatcggc gacggccccg tgctgctgcc cgacaaccac    6120
tacctgagca cccagtccgc cctgagcaaa gaccccaacg agaagcgcga tcacatggtc    6180
ctgctggagt tcgtgaccgc cgccgggatc actctcggca tggacgagct gtacaagtaa    6240
agcggccgcg actcagatcc aagcttcaat tgtggtcact cgacaatcaa cctctggatt    6300
acaaaatttg tgaaagattg actggtattc ttaactatgt tgctcctttt acgctatgtg    6360
gatacgctgc tttaatgcct ttgtatcatg ctattgcttc ccgtatggct ttcattttct    6420
cctccttgta taaatcctgg ttgctgtctc tttatgagga gttgtggccc gttgtcaggc    6480
aacgtggcgt ggtgtgcact gtgtttgctg acgcaacccc cactggttgg ggcattgcca    6540
ccacctgtca gctcctttcc gggactttcg ctttccccct ccctattgcc acggcggaac    6600
tcatcgccgc ctgccttgcc cgctgctgga caggggctcg gctgttgggc actgacaatt    6660
ccgtggtgtt gtcggggaag ctgacgtcct ttccatggct gctcgcctgt gttgccacct    6720
ggattctgcg cgggacgtcc ttctgctacg tcccttcggc cctcaatcca gcggaccttc    6780
cttcccgcgg cctgctgccg gctctgcggc ctcttccgcg tcttcgcctt cgccctcaga    6840
cgagtcggat ctccctttgg gccgcctccc cgcctgctcg agacctagaa aaacatggag    6900
caatcacaag tagcaataca gcagctacca atgctgattg tgcctggcta aagcacaag     6960
aggaggagga ggtgggtttt ccagtcacac ctcaggtacc tttaagacca atgacttaca    7020
aggcagctgt agatcttagc cactttttaa agaaaagggg ggactggaa gggctaattc      7080
actcccaacg aagacaagat ctgctttttg cttgtactgg gtctctctgg ttagaccaga    7140
tctgagcctg ggagctctct ggctaactag ggaacccact gcttaagcct caataaagct    7200
```

```
tgccttgagt gcttcaagta gtgtgtgccc gtctgttgtg tgactctggt aactagagat   7260
ccctcagacc cttttagtca gtgtggaaaa tctctagcag tagtagttca tgtcatctta   7320
ttattcagta tttataactt gcaaagaaat gaatatcaga gagtgagagg acgcgttgga   7380
tgcatagctt gagtattcta tagtgtcacc taaatagctt ggcgtaatca tggtcatagc   7440
tgtttcctgt gtgaaattgt tatccgctca caattccaca caacatacga gccggaagca   7500
taaagtgtaa agcctggggt gcctaatgag tgagctaact cacattaatt gcgttgcgct   7560
cactgcccgc tttccagtcg ggaaacctgt cgtgccagct gcattaatga atcggccaac   7620
gcgcggggag aggcggtttg cgtattgggc gctcttccgc ttcctcgctc actgactcgc   7680
tgcgctcggt cgttcggctg cggcgagcgg tatcagctca ctcaaaggcg gtaatacggt   7740
tatccacaga atcaggggat aacgcaggaa agaacatgtg agcaaaaggc cagcaaaagg   7800
ccaggaaccg taaaaaggcc gcgttgctgg cgttttccca taggctccgc cccctgacg   7860 agcatcacaa aaatcgacgc tcaagtcaga ggtggcgaaa cccgacagga ctataaagat   7920
accaggcgtt tccccctgga agctccctcg tgcgctctcc tgttccgacc ctgccgctta   7980
ccggatacct gtccgccttt ctcccttcgg gaagcgtggc gctttctcat agctcacgct   8040
gtaggtatct cagttcggtg taggtcgttc gctccaagct gggctgtgtg cacgaacccc   8100
ccgttcagcc cgaccgctgc gccttatccg gtaactatcg tcttgagtcc aacccggtaa   8160
gacacgactt atcgccactg gcagcagcca ctggtaacag gattagcaga gcgaggtatg   8220
taggcggtgc tacagagttc ttgaagtggt ggcctaacta cggctacact agaagaacag   8280
tatttggtat ctgcgctctg ctgaagccag ttaccttcgg aaaaagagtt ggtagctctt   8340
gatccggcaa acaaaccacc gctggtagcg gtggtttttt tgtttgcaag cagcagatta   8400
cgcgcagaaa aaaaggatct caagaagatc ctttgatctt ttctacgggg tctgacgctc   8460
agtggaacga aaactcacgt taagggattt tggtcatgag attatcaaaa aggatcttca   8520
cctagatcct tttaaattaa aaatgaagtt ttaaatcaat ctaaagtata tatgagtaaa   8580
cttggtctga cagttaccaa tgcttaatca gtgaggcacc tatctcagcg atctgtctat   8640
ttcgttcatc catagttgcc tgactccccg tcgtgtagat aactacgata cgggagggct   8700
taccatctgg ccccagtgct gcaatgatac cgcgagaccc acgctcaccg gctccagatt   8760
tatcagcaat aaaccagcca gccggaaggg ccgagcgcag aagtggtcct gcaactttat   8820
ccgcctccat ccagtctatt aattgttgcc gggaagctag agtaagtagt tcgccagtta   8880
atagtttgcg caacgttgtt gccattgcta caggcatcgt ggtgtcacgc tcgtcgtttg   8940
gtatggcttc attcagctcc ggttcccaac gatcaaggcg agttacatga tcccccatgt   9000
tgtgcaaaaa agcggttagc tccttcggtc ctccgatcgt tgtcagaagt aagttggccg   9060
cagtgttatc actcatggtt atggcagcac tgcataattc tcttactgtc atgccatccg   9120
taagatgctt ttctgtgact ggtgagtact caaccaagtc attctgagaa tagtgtatgc   9180
ggcgaccgag ttgctcttgc ccggcgtcaa tacgggataa taccgcgcca catagcagaa   9240
ctttaaaagt gctcatcatt ggaaaacgtt cttcggggcg aaaactctca aggatcttac   9300
cgctgttgag atccagttcg atgtaaccca ctcgtgcacc caactgatct tcagcatctt   9360
ttactttcac cagcgtttct gggtgagcaa aaacaggaag gcaaaatgcc gcaaaaaagg   9420
gaataagggc gacacggaaa tgttgaatac tcatactctt cctttttcaa tattattgaa   9480
gcatttatca gggttattgt ctcatgagcg gatacatatt tgaatgtatt tagaaaaata   9540
```

```
aacaaatagg ggttccgcgc acatttcccc gaaaagtgcc acctgatgcg gtgtgaaata    9600
ccgcacagat gcgtaaggag aaaataccgc atcaggaaat tgtaagcgtt aatattttgt    9660
taaaattcgc gttaaatttt tgttaaatca gctcattttt taaccaatag gccgaaatcg    9720
gcaaaatccc ttataaatca aaagaataga ccgagatagg gttgagtgtt gttccagttt    9780
ggaacaagag tccactatta aagaacgtgg actccaacgt caaagggcga aaaaccgtct    9840
atcagggcga tggcccacta cgtgaaccat caccctaatc aagttttttg gggtcgaggt    9900
gccgtaaagc actaaatcgg aaccctaaag ggagcccccg atttagagct tgacggggaa    9960
agccggcgaa cgtggcgaga aaggaaggga agaaagcgaa aggagcgggc gctagggcgc   10020
tggcaagtgt agcggtcacg ctgcgcgtaa ccaccacacc cgccgcgctt aatgcgccgc   10080
tacagggcgc gtccattcgc cattcaggct gcgcaactgt tgggaagggc gatcggtgcg   10140
ggcctcttcg ctattacgcc agctggcgaa aggggggatgt gctgcaaggc gattaagttg   10200
ggtaacgcca gggttttccc agtcacgacg ttgtaaaacg acggccagtg aattgtaata   10260
cgactcacta ta                                                       10272
```

T-Rapa CELLS AS NOVEL EFFECTOR CELL TYPE FOR CHIMERIC ANTIGEN RECEPTOR THERAPY

CROSS-REFERENCE TO RELATED APPLICATIONS

This application claims priority to U.S. Provisional Application No. 62/773,339 filed on Nov. 30, 2018, the contents of which are incorporated by reference in its entirety.

STATEMENT REGARDING FEDERALLY SPONSORED RESEARCH

N/A

BACKGROUND OF THE INVENTION

The field of the invention is chimeric antigen receptor therapy, particularly for the treatment of cancer.

Chimeric antigen receptors (CARs) have recently made a significant impact in the field of cancer immunotherapy. These highly engineered receptors are transduced into autologous patient T cells, giving these T cells the ability to specifically eliminate cells bearing a particular tumour-associated antigen. CAR T cells recognizing the tumour antigen CD19 have now been approved by the FDA for treatment of leukemia and lymphoma, where they have demonstrated striking efficacy in heavily pre-treated, refractory patients who have exhausted all other treatment options. CARs against many other targets are currently being studied in clinical trials.

Despite the landmark successes that these therapies have demonstrated thus far, the field is challenged by several limitations that must be addressed as CAR therapy moves toward the mainstream: overall safety and efficacy in other tumour types are two major issues. Life-threatening toxicities, and even deaths, have been reported in several clinical trials. And, despite the success of CARs in hematological malignancies, equivalent efficacy against solid tumours has yet to be demonstrated.

Clinical protocols for CAR therapy typically include a lymphodepleting preconditioning regimen designed to increase the survival and persistence of the CAR T cells. While this approach is associated with improved clinical responses, it causes damage to healthy cells and has a negative impact on patient quality of life. Furthermore, several patient deaths in clinical trials have been linked to specific preconditioning strategies.

There is a need for improved CAR therapy strategies.

SUMMARY OF THE INVENTION

The present invention overcomes the aforementioned drawbacks by providing T-Rapa cells for the delivery of CAR therapy.

In one aspect, the disclosure provides a method of making a T-Rapa cell expressing a chimeric antigen receptor (CAR). The method can comprise or consist essentially of the steps of: (a) conditioning ex vivo CD3+ T-cells with rapamycin to generate T-Rapa cells; and (b) transducing the T-Rapa cells in vitro with a vector that expresses the CAR to produce CAR-T-Rapa cells. The method can further comprise (c) in vitro expanding the CAR-T-Rapa cells in culture. The T cells of step (a) can be obtained from a subject or suitable donor. The T cells can be obtained from the subject or suitable donor by (i) obtaining a sample from the subject; and (ii) detecting and isolating CD3+T− cells from the sample and culturing the isolated T-cells in vitro. The sample can be a blood sample. The purity of the CD3+ T-cells can be at least 95%. The vector can be a lentiviral vector. Step (a) can comprise culturing the T-cells in chemically defined medium comprising an effective amount of rapamycin to generate T-Rapa cells. The effective amount of rapamycin can be about 0.1 to about 2 micromolar, preferably about 1 micromolar. The chemically defined medium can further comprise recombinant human IL-2 and IFN-α. The CAR can be a CAR specific to a tumor antigen. The CAR can be a CD19 CAR. The method can further comprise maintaining and expanding the CAR-T-Rapa cells in in vitro culture and storing a portion of the CAR-T-Rapa cells for future administration to the subject. The CAR-T-Rapa cells can be stored at or below about −80° C. in suitable storage solution until used.

In another aspect, provided herein is a CAR-T-Rapa cell made by a method provided herein.

In a further aspect, provided herein is a method of treating a subject in need of CAR therapy. The method can comprise or consist essentially of administering an effective amount of a CAR-T-Rapa cell described herein to treat the subject. The subject can have a disease able to be treated with CAR therapy. The disease can be cancer. The cancer can be a hematologic cancer. The cancer can be a solid tumor. Administering can comprise (i) transferring the CAR-T-Rapa cells into the subject, wherein the CAR-T-Rapa cells reduce one or more symptoms of the disease. The CAR-T-Rapa cells can be introduced by intravenous transfusion.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

Figure 1:
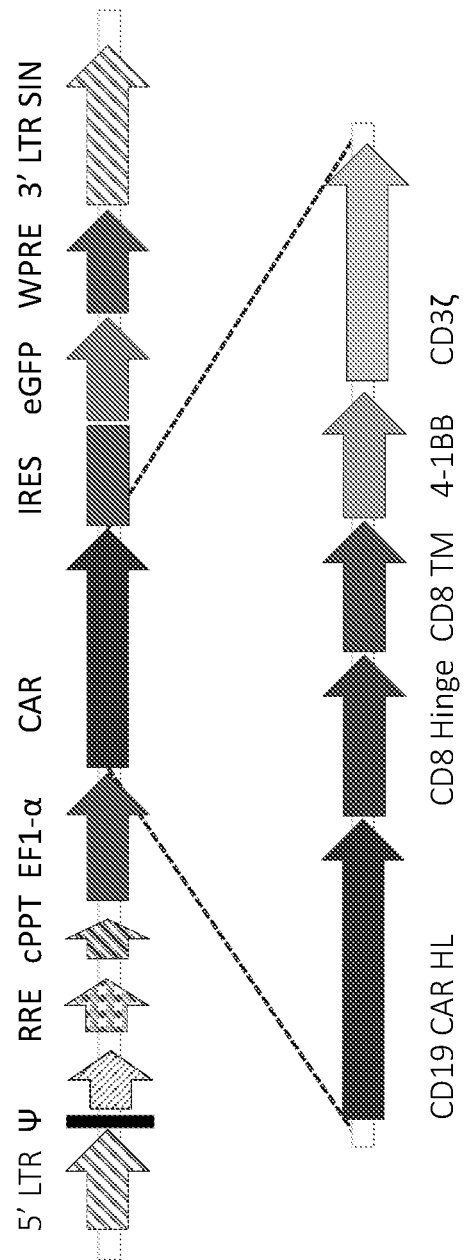
FIG. 1 is a schematic of an exemplary CAR lentivirus construct, particularly a CD19 CAR construct. The LV consists of a 2nd generation CD19 CAR and an IRES eGFP element.

References cited in Figures: [1]. Foley et al., The Journal of Immunology (2005), [2]. Jung et al., Biology of Blood and Marrow Transplantation (2006), [3]. Fowler et al., Blood (2013), [4]. Fowler et al., Biol Blood Marrow Transplant (2016), [5]. Amarnath et al., Autophagy (2010), [6]. Mariotti et al., The Journal of Immunology (2008), [7]. Norelli et al., Nature Medicine (2018), [8]. Barrett et al., Blood (2016)).

DETAILED DESCRIPTION OF THE INVENTION

Despite the landmark successes that CAR therapies have demonstrated thus far, the field is challenged by several limitations: overall safety and efficacy in other tumour types beside hematological malignancies. Besides hematological malignancies, equivalent efficacy against solid tumours has yet to be demonstrated for CARs.

Clinical protocols for CAR therapy typically include a lymphodepleting preconditioning regimen designed to increase the survival and persistence of the CAR T cells. While this approach is associated with improved clinical responses, it causes damage to healthy cells and has a negative impact on patient quality of life. Furthermore, several patient deaths in clinical trials have been linked to specific preconditioning strategies.

Previous studies have shown that T cells grown in rapamycin can be successfully infused back into recipients following a low-dose conditioning regimen. After infusion, these T-Rapa cells have potent effector functions and long-term persistence in recipients.

The present disclosure provides T-Rapa cells that express CARs (CAR-T-Rapa cells). These CAR-T-Rapa cells can then be used in the context of CAR therapy to treat disease, preferably cancers. Not to be bound by any theory, in the context of CAR therapy, T-Rapa cells are believed to require less intensive preconditioning to engraft, reducing toxicities for patients, while having enhanced anti-tumour effects against a broad spectrum of tumour types. T-Rapa cells have not previously been explored as a CAR effector cell. T-Rapa cells can be manufactured from peripheral blood cells of affected patients or normal donors (ND) and can be productively transduced with a vector (e.g., lentiviral vector) expressing a CAR that is able to specifically target a disease, for example, but not limited to, CARs able to target a tumor antigen. The present disclosure provides an improved method that uses cells obtained from the peripheral blood (e.g., T-cells) and can provide a population of CAR-T-Rapa cells that can be stored and infused at any time to boost in vivo circulating anti-antigen (e.g., anti-cancer) T cells. Further, the method requires low, if any, ablation to provide efficient engraftment into the subject.

In one embodiment, the disclosure provides a method of making a T-Rapa cell expressing a chimeric antigen receptor (CAR) (CAR-T-Rapa cell) comprising the steps of: (a) conditioning ex vivo CD3+ T-cells with rapamycin to generate T-Rapa cells; and (b) transducing the T-Rapa cells in vitro with a vector that expresses the CAR to produce the CAR-T-Rapa cells. The method can further comprise in vitro expanding the CAR-T-Rapa cells in culture.

The T cells of step (a) are obtained from a subject or suitable donor. In some embodiments, the subject is the subject in need of CAR therapy, for example, a subject suffering from cancer.

In one embodiment, the T cells are obtained from the subject or suitable donor by (i) obtaining a sample from the subject; and (ii) detecting and isolating CD3+ T-cells from the sample and culturing the isolated T-cells in vitro.

Suitable methods of obtaining T-cells (e.g., CD3+ T-cells) from a subject are known in the art including standard outpatient blood draws or apheresis. In one embodiment, obtaining T-cells comprises detecting and isolating CD3+ T-cells from a peripheral blood sample of a subject or suitable donor. Suitable methods of detecting and isolating CD3+ T-cells from peripheral blood are known in the art and include, but are not limited to, for example, flow cytometric cell sorting, including fluorescence-activated cell sorting (FACS), or magnetic separation with the use of magnetic beads that recognize T-cells, including magnet-assisted cell sorting (MACS). In suitable embodiments, antibodies specific to CD3 that may be, in some examples, attached to magnetic beads, are used to separate CD3+ T-cells from other cells found in peripheral blood. Alternatively, negative selection can be used to deplete the CD3− cells, allowing for the enrichment of CD3+ cells. An advantage of the methods of the current technology are that CD3+ T-cells for use in the methods can be obtained from a peripheral blood sample obtained from an outpatient blood draw and do not require any priming or other treatment steps prior to the isolation of the peripheral blood. In some embodiments, the isolated CD3+ T-cells are at least about 70% CD3+(70% pure), more preferably at least about 75% CD3+(75% pure), alternatively at least about 80% CD3+(80% pure), alternatively at least about 85% CD3+(85% pure), at least about 90% CD3+(90% pure), at least about 95% CD3+(95% pure).

In some embodiments, once the CD3+ T-cells are isolated, the CD3+ T-cells are cultured in vitro to expand the cells.

In some embodiments, once isolated, the isolated CD3+ T-cells are conditioned/treated with rapamycin to form T-Rapa cells. Suitably, the T-cells may be conditioned/treated with rapamycin before transduction with the vector encoding the CAR. Methods of conditioning T-cells to form T-Rapa cells is known in the art and described in Fowler et al. 2013, the contents of which are incorporated by reference in its entirety. Suitably, the isolated T-cells are cultured in chemically defined medium comprising cytokines and rapamycin in a suitable amount to transform the T-cells into rapamycin resistant T-cells (T-Rapa cells).

Suitable amounts of rapamycin to transform T-cells into T-Rapa cells include, but are not limited to, a concentration of about 0.1 micromolar to about 2 micromolar, (0.1-2 µM), alternatively from about 0.8-1.5 micromolar. Lower concentrations of rapamycin such as 0.1 micromolar can be used; however, lowering the concentration of rapamycin can deteriorate the ability to grow rapamycin-resistant T-cells, and as such, a preferred concentration of rapamycin is about 1 micromolar. Increasing the rapamycin concentration above 1 micromolar has limited feasibility because the drug is not fully solubilized in conventional media above this concentration. As such, concentrations around 1 micromolar are optimal for achievement of the rapamycin resistance (T-Rapa) phenotype.

In some embodiments, the T-cells are cultured in medium with rapamycin and cytokines able to produce T-Rapa cells with a Th1/Tc1 phenotype (T Rapa1, see, e.g., Jung et al., Biology of Blood and Marrow Transplantation (2006), incorporated by reference in its entirety.) In one suitable embodiment, the T-cells are cultured in medium comprising recombinant human IL-2 and IFN-α. In a preferred embodiment, the T-cells are cultured in medium comprising about 5-20 IU/mL IL-2 and about 5,000-15,000 IU/mL IFN-α, preferably about 10,000 IU/mL IFN-α.

In some embodiments, step (a) comprises culturing the T-cells in chemically defined medium comprising an effective amount of rapamycin to generate T-Rapa cells. Ex vivo treatment with rapamycin elicits numerous changes in T-cells (e.g., CD3+ T-cells) that, in sum, endow them with a pro-engraftment and anti-apoptotic phenotype. These cells are termed T-Rapa cells. More about T-Rapa cells can be found in Fowler et al. ("Phase 2 clinical trial of rapamycin-resistant donor CD4+Th2/Th1 (T-Rapa) cells after low-intensity allogeneic hematopoietic cell transplantation," Blood (2013) 11:121 (15):2864-2874), the contents of which are incorporated by reference in its entirety. Successful allotransplantation of donor T-Rapa cells requires less host conditioning (lymphocyte-specific, myeloid sparing) that results in the creation of sufficient immune space for T-cell engraftment while causing minimal host myeloid cell depletion.

Once T-Rapa cells are derived, the T-Rapa cells are transduced in vitro with a vector that allows expression of the CAR.

Suitable CARs will depend on the disease or disorder being treated, for example, the specific type of cancer to be treated. In one embodiment, the CAR may be specific to a tumor-specific antigen. CARs may be specific to a target antigen under clinical evaluation for CAR therapy as reviewed by Robyn A. A. Oldham & Jeffrey A. Medin (2017), Expert Opinion on Biological Therapy, DOI: 10.1080/14712598.2017.1339687 (see, for example, Tables 3 and 4). Exemplary targets include, without limitation, CD19, BCMA, CD133, CD171, CD20, CD30, CD33, CEA, CLL1 (C-C Motif Chemokine Ligand 1), CLEC1A (C-Type Lectin Domain Family 1, Member A), EGFR, ERBB2, GD2, Kappa Ig (Igκ), IL13RA2, Mesothelin, MUC1, PSMA, and CD22.

In one embodiment, the CAR is a CD30 CAR, a CLL1 CAR, or a CLEC1A CAR.

In one embodiment, the CAR is a CD19 CAR that targets B cells. In some embodiments, the CD19-CAR is able to treat leukemias and lymphomas, for example, B-cell lymphomas.

In one embodiment, the vector is a lentiviral vector able to express a CD19-CAR (e.g., SEQ ID NO:2 or a sequence with at least 75% identity to SEQ ID NO:2) in T-Rapa cells, for example, the lentiviral vector of SEQ ID NO:3 or a sequence with at least 75% identity to SEQ ID NO:3. The present disclosure is not limited to this vector or CAR, and other vectors and suitable CARs known in the art or able to be derived are contemplated for use in the present methods of the disclosure.

The CAR can be expressed in the T-Rapa cells by methods known in the art, including the transduction of a vector able to express the CAR. Suitable vectors are known in the art and contain the necessary elements in order for the gene encoded within the vector to be expressed in the host cell. The term "vector" refers to a nucleic acid molecule capable of transporting another nucleic acid to which it has been linked. One type of vector is a "plasmid", which refers to a circular double stranded DNA loop into which additional DNA segments may be ligated, specifically exogenous DNA segments encoding the targeted protein. Another type of vector is a viral vector, wherein additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome (e.g., lentiviral vectors). Moreover, certain vectors are capable of directing the expression of exogenous genes to which they are operatively linked. Such vectors are referred to herein as "recombinant expression vectors" (or simply, "expression vectors" or "vectors"). In general, vectors of utility in recombinant DNA techniques are often in the form of plasmids. In the present specification "vector" include expression vectors, such as viral vectors (e.g., replication defective retroviruses (including lentiviruses), adenoviruses and adeno-associated viruses), which serve equivalent functions.

The vectors are heterogeneous exogenous constructs containing sequences from two or more different sources. Suitable vectors include, but are not limited to, plasmids, expression vectors, lentiviruses (lentiviral vectors), adeno-associated viral vectors (rAAV) among others and includes constructs that are able to express the CAR (e.g., CD19 CAR). A preferred vector is a lentiviral vector. Suitable methods of making lentiviral vector particles are known in the art. While specific lentiviral vectors have been used in the examples, the vectors are not limited to these embodiments and any lentiviral vectors or other vectors capable of expressing the CAR are contemplated for use in the practice of the current invention.

A vector can preferably transduce, transform or infect a cell, thereby causing the cell to express the nucleic acids and/or proteins encoded by the vector (e.g., the CAR).

Suitable methods of cloning the CAR, for example, the CD19-CAR (SEQ ID NO:1 or a sequence with at least 75% identity to SEQ ID NO:1 and is able to bind CD19) into an exogenous expression vector (for example a lentiviral vector) are known in the art for producing functional vector to engineer T-Rapa cells to express CAR for treatment of disease.

Suitable amounts of lentivirus able to transduce T-Rapa cells include, for example, using a MOI (multiplicity of infection) of 1-100, preferably an MOI of 1-30, alternatively 1-60. The T-Rapa cells may be exposed to the lentivirus for 10-24 hours, suitably about 12-16 hours. Cytokines may be added to the culture medium during transduction. After transduction, the cells can be either transferred back into the patient, expanded in culture, or cryopreserved for later transplantation, or a combination of the above. In some instances, the transduced cells may be cultured for a number of days before being transferred or cryopreserved. Suitable methods of cryopreservation are known in the art.

In some embodiments, the derived CAR-T-Rapa cells are maintained and expanded under in vitro culture conditions. Suitable methods of maintaining and expanding the CAR-T-Rapa cells in in vitro culture are known in the art. Further, the CAR-T-Rapa cells of the present disclosure may be stored for future administration to the subject. Suitable methods of storing the CAR-T-Rapa cells are known in the art.

In some embodiments, the transduced T-Rapa cells are expanded in culture and cryopreserved at various stages of culture. Suitable methods of cryopreservation include, but are not limited to, suspending the cells in a cryopreservation medium and storing the cells at −80° C. to −196° C., preferably below −80° C. Suitable cryopreservation media are known in the art and may comprise some combination of base medium, cryopreservative (e.g., dimethylsulfoxide (DMSO), glycerol) and a protein source. For example, a suitable cryopreservation medium may comprise complete medium and 10% glycerol, complete medium containing 10% DMSO, or 45% cell-conditioned medium with 45% fresh medium and 10% glycerol or DMSO. In alternative embodiments, the cryopreservation medium may be serum free, for example, comprises 46.25% cell-conditioned serum-free medium with 46.25% fresh serum-free medium and 7.5% DMSO. The cryopreservation components held reduce or prevent the formation of ice crystals during the freezing process to retain viability of the cells. In another suitable embodiment, the T cells are frozen using cryopreservation medium comprising 90% human serum and 10% DMSO; or 40% medium, 50% human serum and 10% DMSO. Other suitable ranges therebetween are contemplated to be within the scope of the present disclosure.

Suitable chemically defined medium for culturing T-cells are known in the art and include, but are not limited to, commercial nutrient-rich media such as X-Vivo 20. Suitably, the chemically defined medium is further supplemented with 5% human AB and cytokines. Preferably, in one embodiment, recombinant human IL-2 (rhu IL-2) are used to supplement the medium. Suitable amount of the recombinant cytokines include about 10-100 IU/mL of IL-2, preferably about 20 IU/mL of IL-2.

In some embodiments, the transduced CAR-T-Rapa cells are expanded in vitro. During expansion, the CAR-T-Rapa cells may be cultured in chemically defined medium supplemented with cytokines and human AB serum as described herein. Suitably, the CAR-T-Rapa cells may be cultured for at least one day, and suitably may be cultured for at least 2 weeks, alternatively at least 4 weeks, alternatively at least 6 weeks.

The CAR-T-Rapa cells may be maintained and expanded in vitro in culture for at least 5 passages, alternatively at least 10 passages, alternatively at least 15 passages, alternatively at least 20 passages. The transduced T-Rapa cells may be cryopreserved at any passage after transduction.

The present disclosure also contemplates compositions comprising the CAR-T-Rapa cells described herein. In some embodiments, the compositions further comprising a pharmaceutically acceptable carrier. A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced and in which maintain the CAR-T-Rapa cell viability until administration. Typically, buffered saline or other saline solutions are physiologically acceptable carriers. Water is not contemplated as a suitable physiologically acceptable carrier. In some embodiments, additional components may be added to preserve the structure and function including viability of the CAR-T-Rapa cells, and are physiologically acceptable for administration to a subject.

The CAR-T-Rapa cells described herein may be used in methods for providing CAR therapy, preferably therapy to a patient with cancer. In some embodiments, methods of treating a subject in need of CAR therapy, e.g. a subject having cancer are provided. The methods comprise administering an effective amount of the CAR-T-Rapa cells described herein to treat a subject.

In a preferred embodiment, the subject has cancer and the CAR-T-Rapa cells are provided in an amount effective to reduce one or more symptoms of the cancer. Suitable methods of administering the transduced T-Rapa cells are known in the art, and include, but are not limited to, intravenous injection and transfusion.

The transduced T-Rapa cells may be administered at least once, and suitably will be administered at subsequent times to elicit an anti-cancer response to treat one or more symptoms of the cancer.

In one embodiment, the cancer is a hematological cancer, for example, leukemia and lymphoma, including B cell lymphoma.

The present compositions may be used to treat cancer. The term "cancer" or "tumor" are used interchangeably herein to refer to uncontrolled cell growth within a subject. The compositions, methods and kits of the present invention may be used to treat any cancer or metastasis thereof. The methods of the present disclosure can be used to treat any cancer, any metastases thereof, and any chemo-residual growth thereof, including, but not limited to, carcinoma, lymphoma, blastoma, sarcoma, and leukemia. Suitable cancers able to be treated by the compositions, methods and kits described herein include, but are not limited to, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulvar cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, and peripheral neuroepithelioma.

The term "subject" or "patient" are used interchangeably and refer to a mammalian subject, for example, a mouse, a rat, a monkey, a human, etc. In a preferred embodiment, the subject is a human. It is contemplated that the subject or patient may have already been treated with one or more therapies for the cancer before undergoing the treatment contemplated herein.

For purposes of the present invention, "treating" or "treatment" describes the management and care of a subject for the purpose of combating the disease, condition, or disorder. Treating includes the administration of the CAR-T-Rapa cells to prevent the onset of the symptoms or complications, alleviating the symptoms or complications, or eliminating the disease, condition, or disorder. Treating also encompasses therapeutic and palliative treatment. The aim of treatment includes the alleviation or prevention of symptoms, slowing or stopping the progression or worsening of a disease, disorder, or condition and/or the remission of the disease, disorder or condition. In certain embodiments, the treatment comprises anti-cancer therapy and/or treatments. The term "treatment" can be characterized by at least one of the following: (a) the reducing, slowing or inhibiting the growth of cancer and cancer cells, including slowing or inhibiting the growth of metastatic cancer cells; (b) preventing the further growth of tumors; (c) reducing or preventing the metastasis of cancer cells within a subject; (d) reducing or ameliorating at least one symptom of cancer. In some embodiments, the optimum effective amount can be readily determined by one skilled in the art using routine experimentation.

The term "effective amount" or "therapeutically effective amount" refers to an amount sufficient to effect beneficial or desirable biological and/or clinical results. That result can be reducing, inhibiting or preventing the growth of cancer cells, reducing, inhibiting or preventing metastasis of the cancer cells or invasiveness of the cancer cells or metastasis, or reducing, alleviating, inhibiting or preventing at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptom of the cancer or metastasis thereof. Such effective treatment may, e.g., reduce patient pain, reduce the tumor size or number of cancer cells, may reduce or prevent metastasis of a cancer cell, or may slow cancer or metastatic cell growth. The CAR-T-Rapa cells described herein are believed to have reduced side effects than conventional CAR-T cells, e.g., lower pro-inflammatory side effect (e.g., lower INF-γ response).

In some embodiments, kits for carrying out the methods described herein are provided. The kits provided may contain the necessary components with which to carry out one or more of the above-noted methods. In one embodiment, a kit for treating cancer is provided. In one embodiment, the kit comprises a vector encoding a CAR and instructions for producing CAR-T-Rapa cells. In another embodiment, the kit comprises suitable T cells and rapamycin or T-Rapa cells for producing CAR-T-Rapa cells and instructions for transducing the CAR into said cells.

"Percentage of sequence identity" or "sequence similarity" is determined by comparing two optimally aligned sequences over a comparison window, wherein the portion of the polynucleotide sequence in the comparison window may comprise substitutions, or additions or deletions (i.e., gaps) as compared to the reference sequence (which does not comprise substitutions, additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "similarity" of polypeptide or polynucleotide sequences means that a polypeptide or polynucleotide comprises a sequence that has at least 75% sequence identity. Suitable sequence similarity allows for small changes in the transgene that do not affect the function of the protein expressed by the transgene. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using programs such as BLAST using standard parameters. These values can be appropriately adjusted to determine corresponding identity of proteins encoded by two nucleotide sequences by taking into account codon degeneracy, amino acid similarity, reading frame positioning and the like.

Suitable methods of producing a population of transduced CAR-T-Rapa cells are provided herein.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The invention will be more fully understood upon consideration of the following non-limiting examples.

EXAMPLES

Example 1: CAR Expressing T-Rapa Cells

Introduction: Despite some striking clinical success thus far, chimeric antigen receptor (CAR) engineered cells have the potential to cause severe side effects. Neurotoxicity and cytokine release syndrome (CRS), the latter characterized by increased levels of cytokines such as IL-6, IFN-γ, and MCP-1, are common adverse events associated with CAR therapy. Lymphodepleting preconditioning regimens are associated with improved clinical responses to CAR therapy, yet lymphodepletion has also been identified as a risk factor for CRS. Understanding and management of these toxicities has improved significantly, however these conditions are challenging to treat and can be life-threatening. The ability to limit or prevent initiation of CRS would greatly improve the safety of CAR therapy.

Previous clinical trials have shown that T-Rapa cells (patient T cells that have been grown ex vivo in rapamycin) can be successfully infused back into autologous recipients after a low-dose conditioning regimen. After infusion, these T-Rapa cells have potent effector functions and demonstrate long-term persistence. This Example demonstrates that T-Rapa cells, engineered by lentivirus-mediated gene transfer to express a CAR, particularly an anti-CD19 CAR, are just as effective at killing tumor cells as similarly engineered pan T cells but produce dramatically less pro-inflammatory cytokines, such as IFN-γ, for example.

Figure 2:
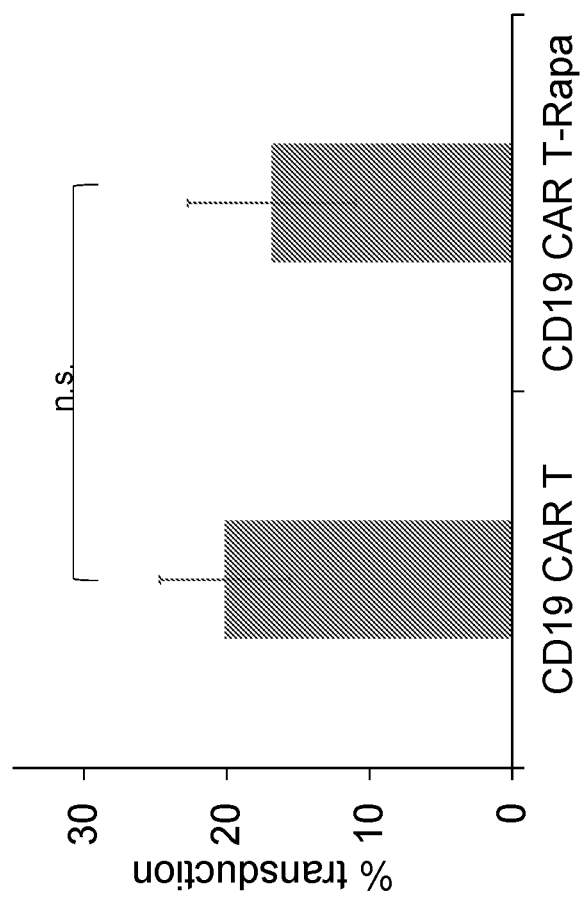
FIG. 2 is a bar graph demonstrating both T and T-Rapa cells transduce equivalently well with the CD19 CAR IRES eGFP LV. T-test p=0.6.

Methods: Human CD3+ cells were treated with rapamycin for 3 days in the presence of IFN-α and IL-2 to produce T-Rapa cells having a Th1/Tc1 phenotype. An anti-CD19-41BB-CD3ζ CAR construct (SEQ ID NO:1 (DNA) and SEQ ID NO:2 (protein)) was subcloned into a lentiviral vector backbone containing an IRES-eGFP element (SEQ ID NO:3) (See FIG. 1). Vector was prepared and used to transduce T or T-Rapa cells (FIG. 2). On day 3 of cell culture with rapamycin, cells were washed and resuspended in X-Vivo with human AB serum and IL-2 at a cell density of about $1.5 \times 10^6$ cells/0.5 ml with lentivirus at an MOI of 6, and protamine sulfate at 8 ng/ml. An equal volume of fresh media was added 6 hours after infection. After 16 hours, the cells were washed and replated with fresh lentivirus supernatant. The following day, cells were washed and replated in fresh media. Lentivirus transduced T-Rapa cells were harvested on day 6 of cell culture. Transgene expression was assessed by FACS for eGFP and Protein L staining for the CAR.

CAR-T cells were then expanded using CD3/CD28 beads in the presence of IL-2. The expanded cells were used in assays including FACS assessment of T cell phenotype, co-culture assays, and $^{51}$Cr release assays in comparison with non-rapamycin treated CAR T cells and non-transduced controls.

Figures 3A, 3B, 3C, 3D, 3E:
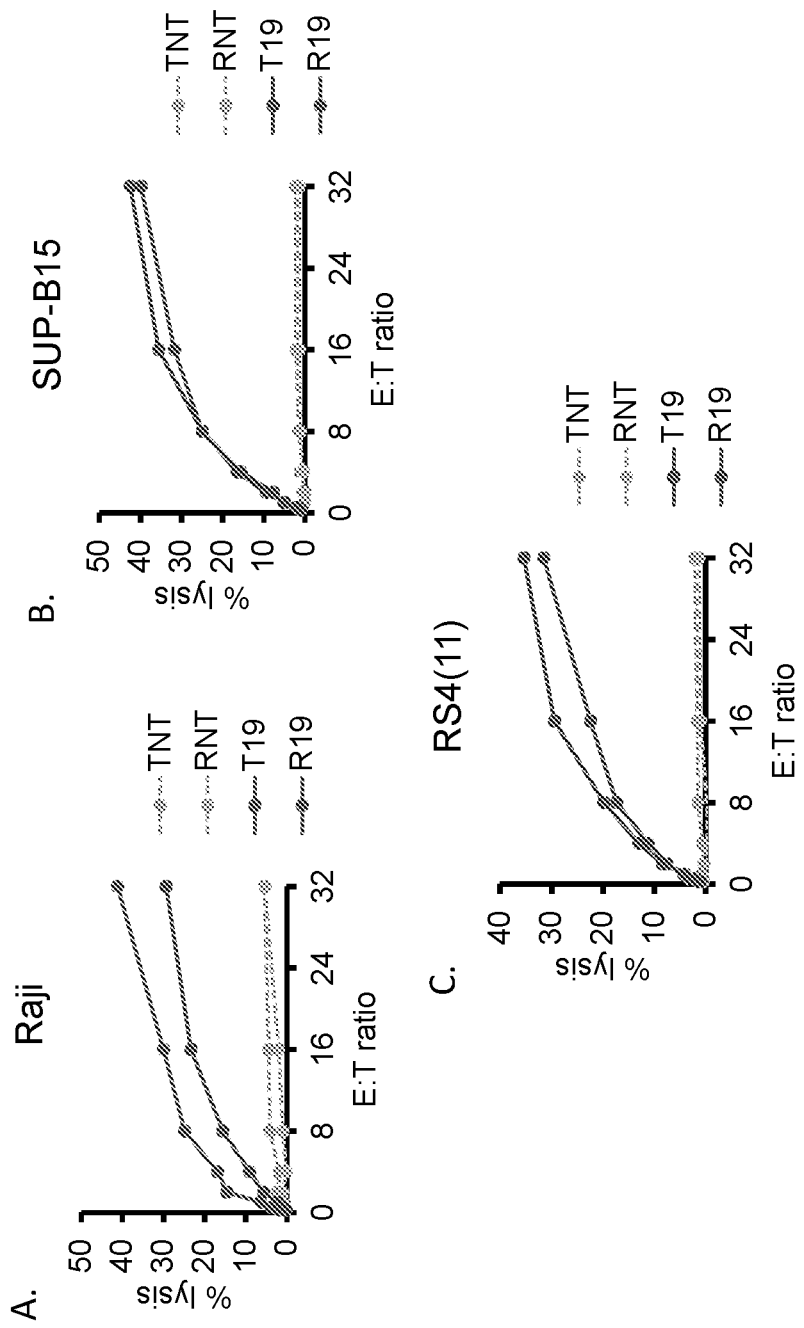
FIGS. 3A-3E are line graphs demonstrating both CD19 CAR-T and CD19 CAR-T-Rapa cells kill CD19+ target cells (A. Raji cells, B. SUP-B15 cells, C. R54(11) cells, and D. OCIAML2 cells transduced with human CD19) effectively, while sparing CD19-cells (E. OCIAML2 cells). Non-transduced (NT) T and T-Rapa cells are incapable of killing either CD19+ or CD19− cells. E:T ratio shown is for total T cells, and not adjusted for % transduction with CAR.
Figures 3A, 3B, 3C, 3D, 3E:
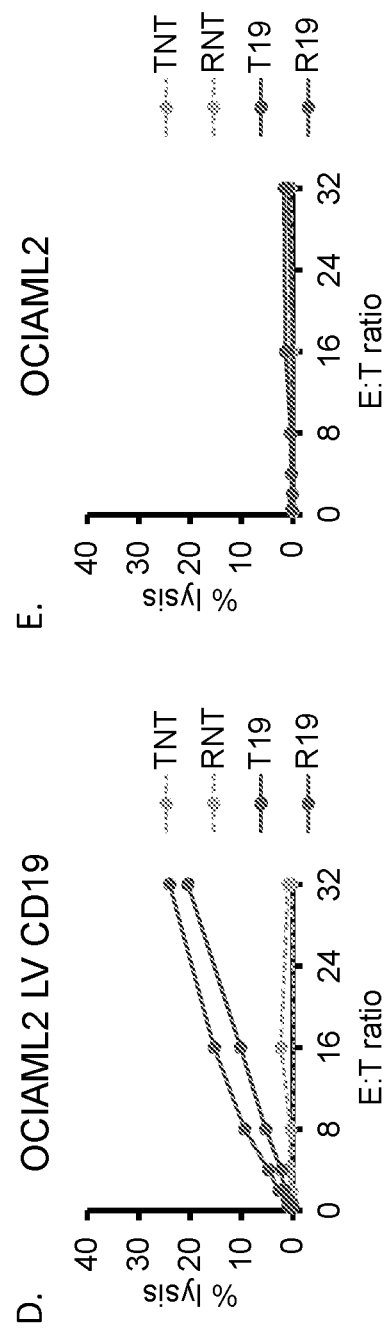
Figures 4A, 4B:
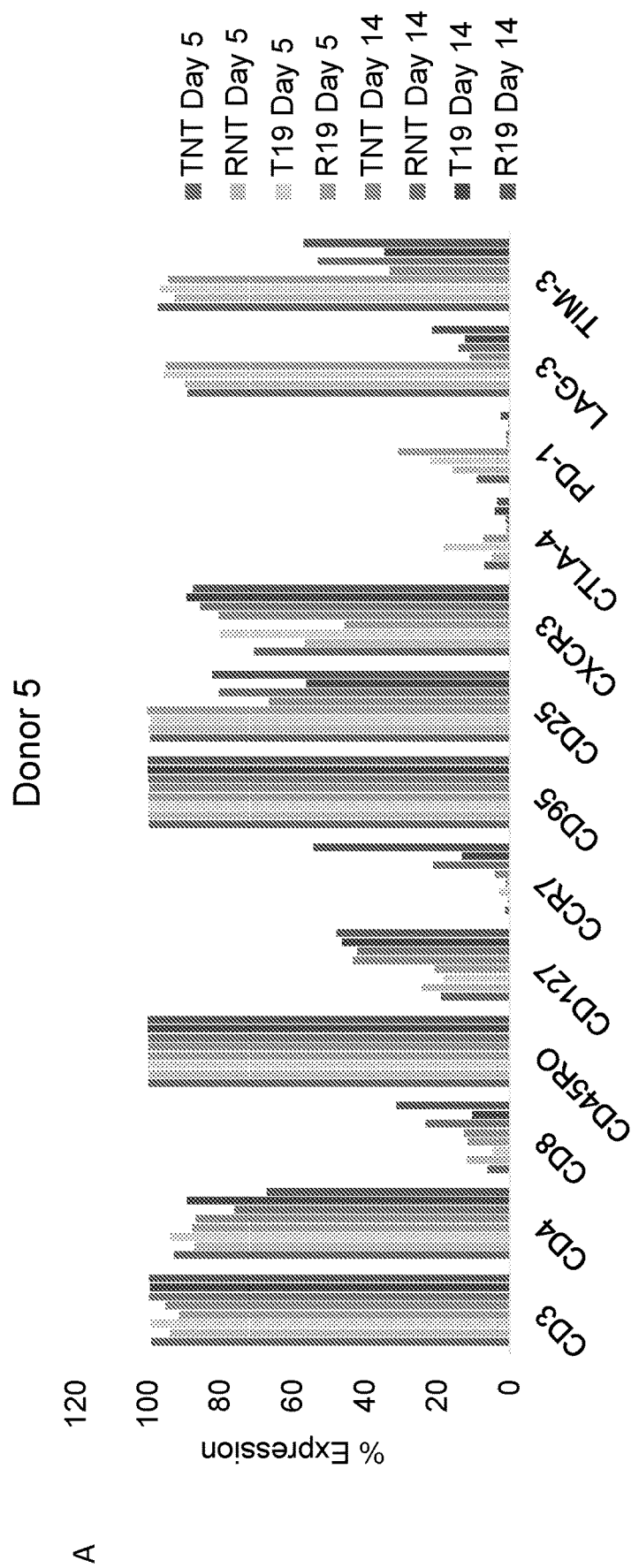
FIGS. 4A-4B demonstrate the cell surface phenotype of NT or CART and T-Rapa cells from two donors which was assessed by FACS after 5 and 14 days in culture post-thaw. There is some variability between donors; donor 5 (A.) and donor 2 (B.) are shown. All cell types are CD45RO+, CD95+, & CD127+, consistent with a memory phenotype. T-Rapa cells have higher expression of CCR7, as reported in literatures, indicating a TCM phenotype. There is variability in expression of CD4, CD8, CD25, CTLA-4, PD-1, LAG-3, and TIM-3, however these factors appear to be impacted primarily by timepoint (Day 5 vs. Day 14) rather than by transduction with CD19 CAR or by Rapa resistance.
Figures 4A, 4B:
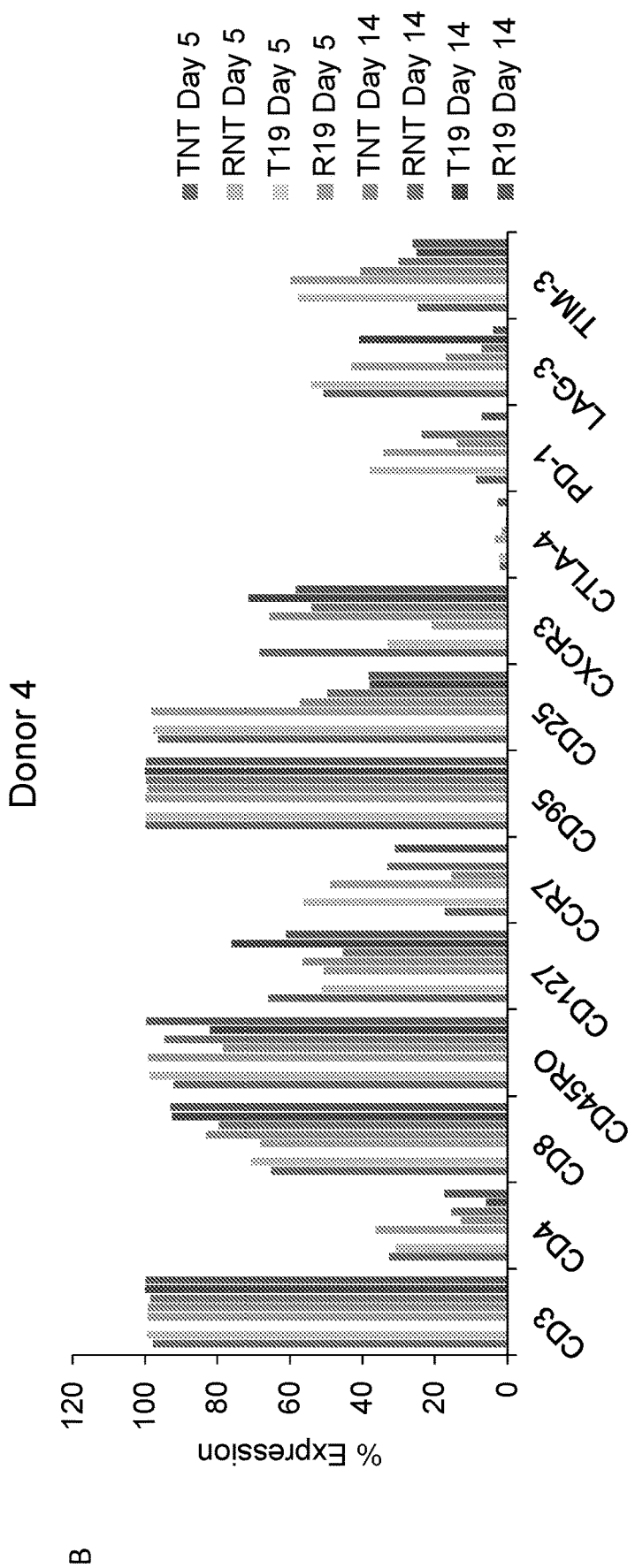
Figure 5:
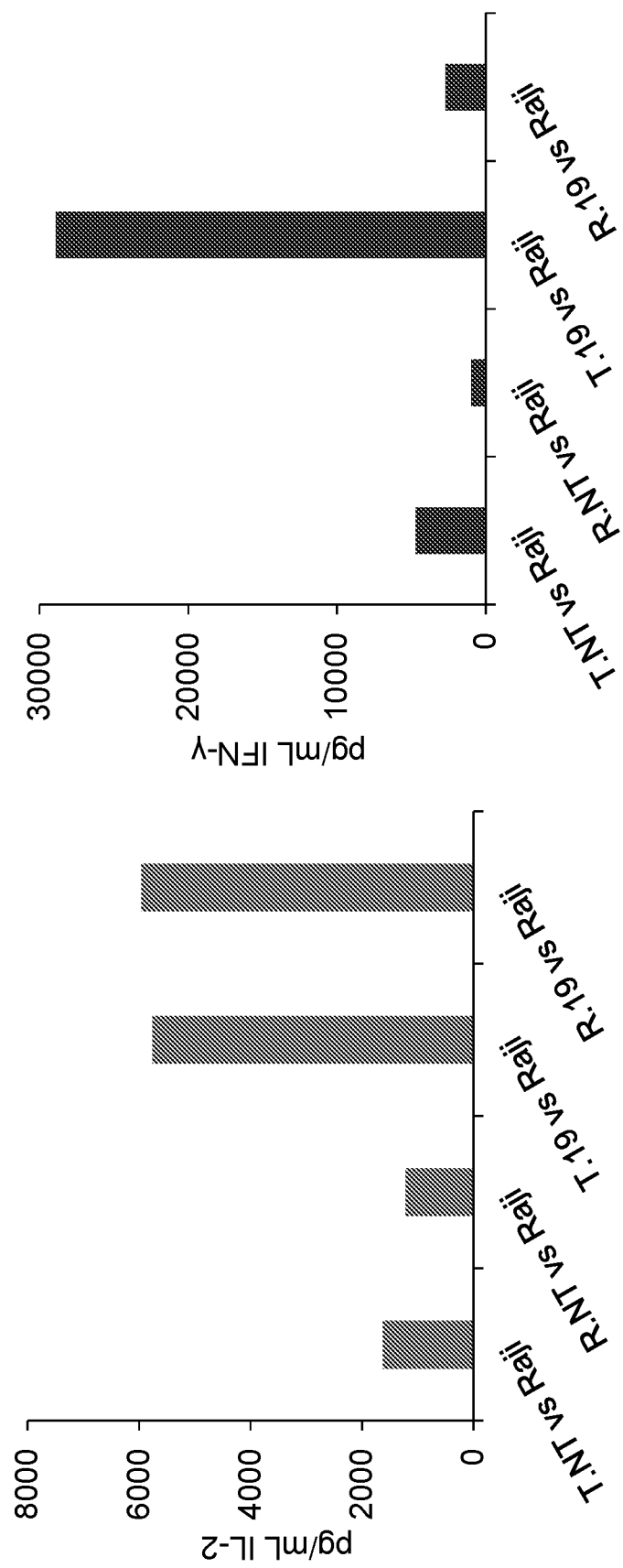
FIG. 5 depicts IL2 and INF-γ response in tested cells. NT or CART & T-Rapa cells were co-cultured for 24 h with CD19+ Raji cells. Only CAR-transduced T and T-Rapa cells produce IL-2 in response to Raji cells. However, CAR-T-Rapa cells produce significantly less IFN-γ.
Figures 6A, 6B, 6C:
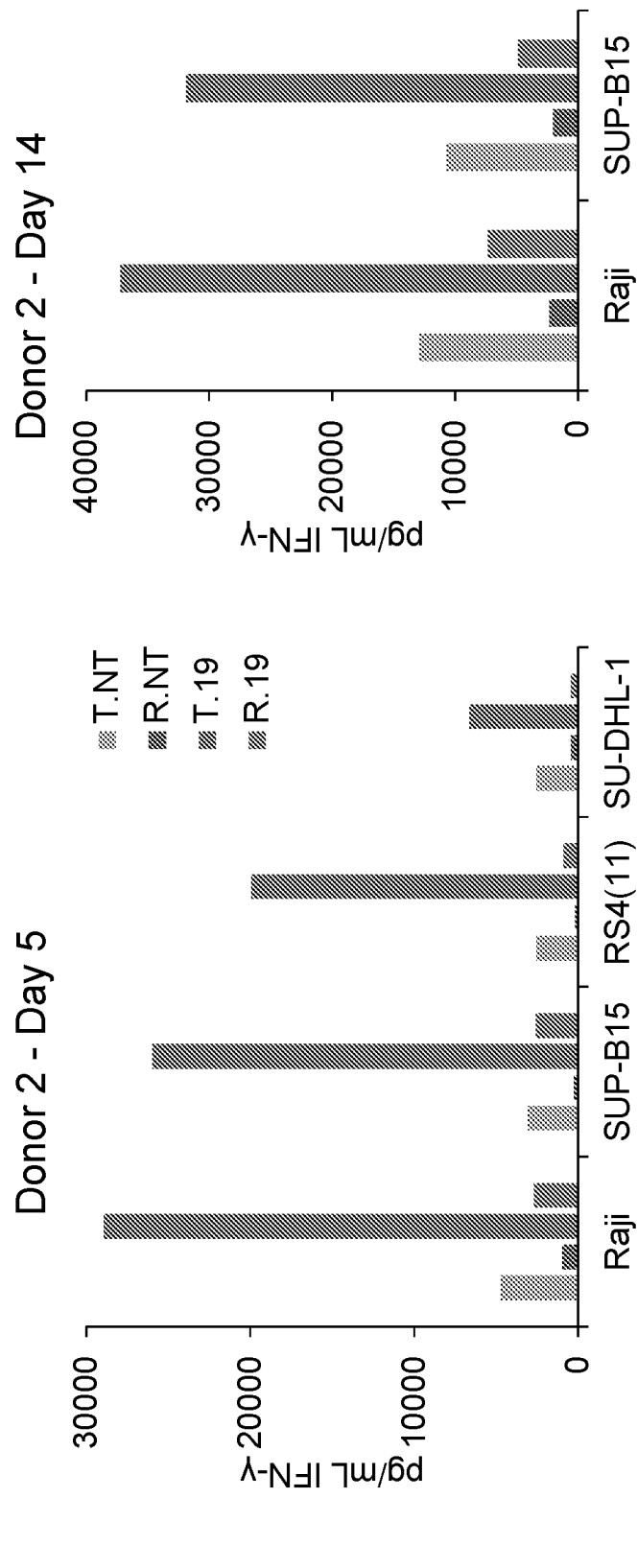
FIGS. 6A-6C demonstrate immune response produced by CAR-T-Rapa cells. To confirm and expand on the previous results, NT or CAR T & T-Rapa cells from multiple donors were cultured for 5 and 14 days post-thaw, followed by co-culture for 24 h with CD19+ Raji, SUP-B15 or R54(11) cells, or CD19− SU-DHL-1 cells. There is variability between donors (donor 2 (6A), donor 3 (6B) and donor 4 (6C)) and target cell lines, however, in all conditions CAR-T cells produce significantly more IFN-γ than CAR-T-Rapa cells, or NT T & T-Rapa controls.
Figures 6A, 6B, 6C:
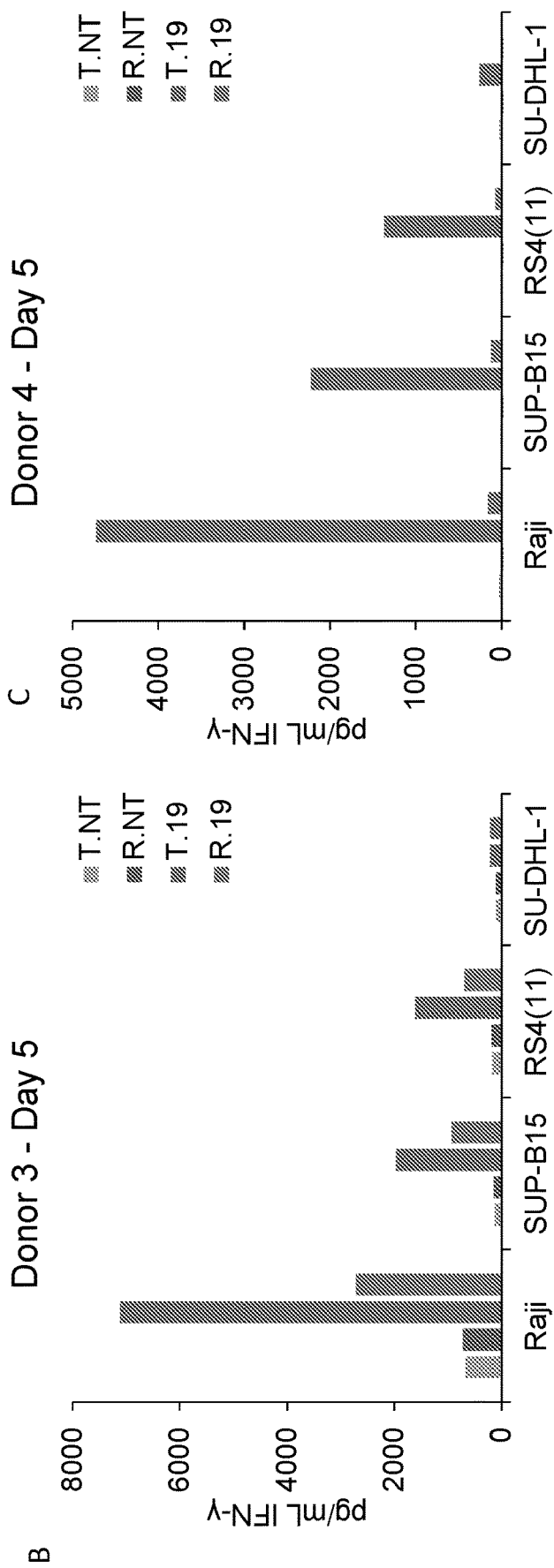
Figures 7A, 7B, 7C, 7D, 7E, 7F:
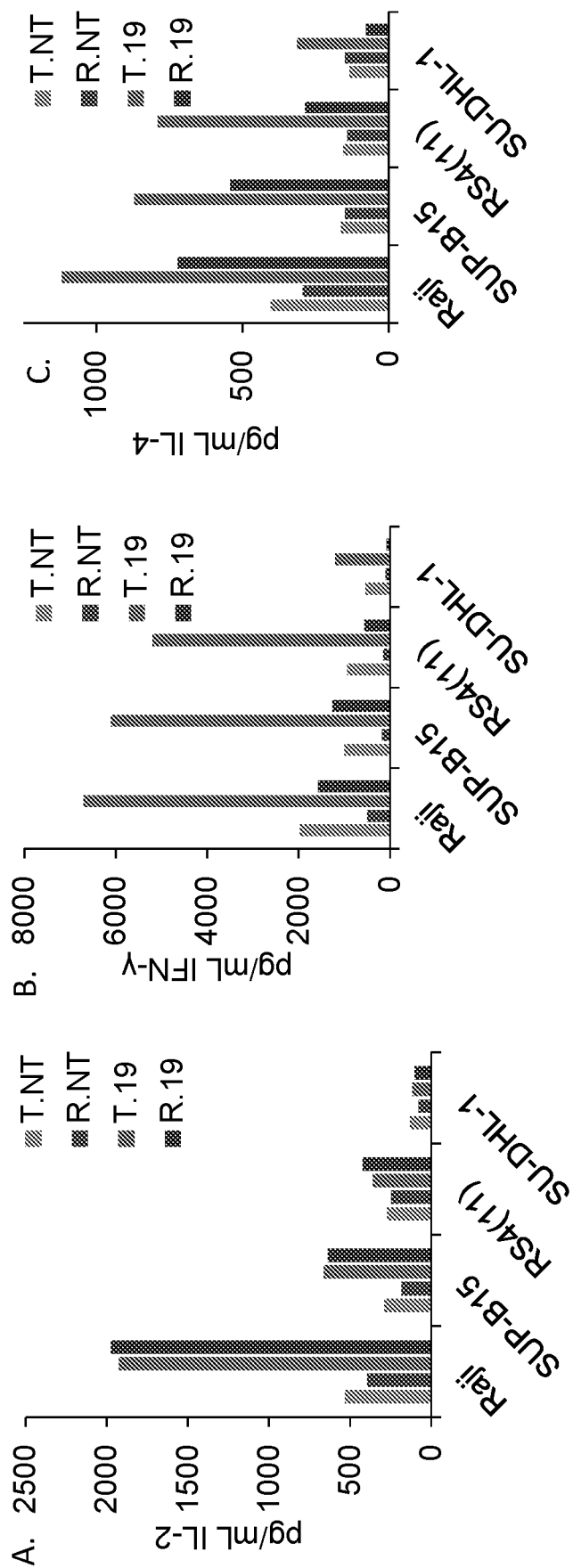
FIGS. 7A-7F demonstrate cytokine production. Supernatants from T & T-Rapa co-culture experiments shown in FIGS. 6A-6C were also analyzed by Luminex for presence of a panel of cytokines, including IL-2, IFN-γ, IL-4, TNF-α, GM-CSF, and IL-6 (7A.-7F.). Donor 2, Day 5 results are shown. The production of IL-2 is again shown to be consistent between CAR-T and CAR-T-Rapa cells. IFN-γ production from CAR-T-Rapa cells is again significantly lower in comparison to CAR-T cells. Production of IL-4, TNF-α, and GM-CSF are also lower from CAR-T-Rapa cells. Production of IL-6 is low overall, consistent with reports that monocytes, not T cells, are the source of IL-6 during cytokine release syndrome (CRS)[7,8].
Figures 7A, 7B, 7C, 7D, 7E, 7F:
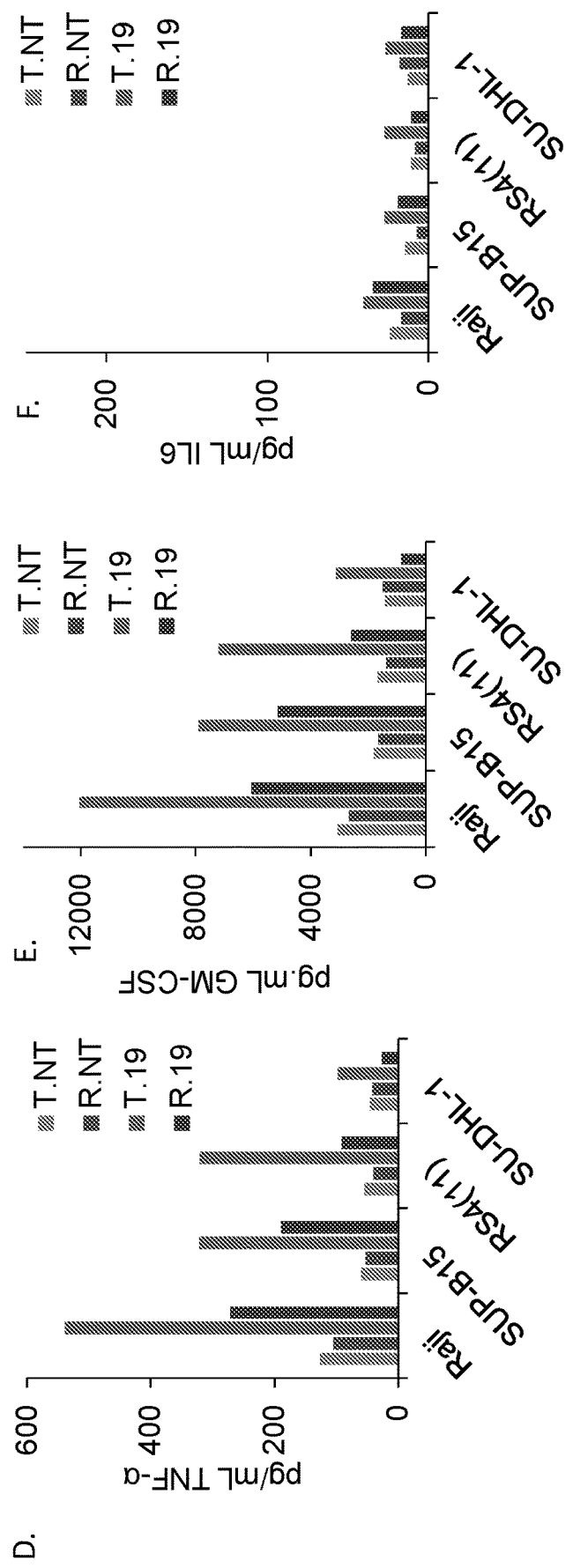

Results: Following transduction and expansion, similar eGFP and CAR expression levels were found in T and T-Rapa cells transduced at the same MOI (FIG. 2). CAR-T and CAR-T-Rapa cells developed from multiple independent T cell donors exhibited similar phenotypes at days 5 and 14 post-thaw, as determined by analyses of T-cell subset and exhaustion markers including CD45RO, CD127, CCR7, CD95, CD25, CXCR3, CTLA-4, PD-1, LAG-3, and TIM-3 (FIG. 4). All cell types were CD45RO$^+$, CD95$^+$, and CD127$^+$, which is consistent with a memory phenotype. T-Rapa cells have higher expression of CCR7, indicating a $T_{CM}$ (T central memory) phenotype. Both CAR-T and CAR-T-Rapa cells exhibited comparable levels of cytotoxicity against CD19+ Raji, SUP-B15 and RS4;11 cancer cell lines after coculture for 4 hours in a $^{51}$Cr release assay (FIG. 3). Further, both T and T-Rapa CAR cells produced similar amounts of IL-2 following a 24-hour coculture with CD19+ Raji, SUP-B15 and RS4;11 cancer cell lines, as measured by ELISA (FIG. 5). Interestingly, CAR-T-Rapa cells produced significantly less IFN-γ than CAR-T cells after 24 hours of coculture with CD19+ tumor cells (FIG. 6 and FIG. 7). CAR-T-Rapa cells also produced less TNF-alpha and GM-CSF (FIG. 7). This observation was consistent for CAR-T and CAR-T-Rapa cells assessed at both day 5 and day 14 post-thaw.

Conclusions: T-Rapa cells can be successfully transduced with a CAR vector, and show comparable T cell subset, exhaustion phenotype, and cytotoxicity to CAR-T cells that have not been treated with rapamycin. In spite of these similarities, when challenged with CD19+ tumor cells, CAR-T-Rapa cells produced less IFN-γ, TNF-alpha and GM-CSF than CAR-T cells. Decreased production of pro-inflammatory cytokines, such as IFN-γ, may reduce the risk and severity of CRS, improving the safety of CAR therapy.

Example 2: Obtaining T Cells for Making T-Rapa Cells

T-Rapa cells can be made from T cells obtained from the peripheral blood of a patient or a donor. CD3 cells were positively selected from the blood (Miltenyi; CliniMACS® device, or laboratory equivalent) and co-stimulated (tosylated magnetic beads [Dynal] conjugated with GMP-grade anti-CD3 [OKT3; Ortho] and GMP-grade anti-CD28 9.3 antibodies [3:1 bead:cell ratio]).

Purified CD3+ cells are cultured in X-VIVO 20 media (Lonza), 5% human plasma or human AB serum, recombinant human (rhu) IL-2 (20 I.U./mL; Chiron), INF-α and rapamycin (1 μM), and anti-CD3/CD28 beads (3:1).

After 3 days, T-cells are washed and transduced at an MOI of 1-60 with lentivirus vector carrying the CAR transgene. After 16 hours, T-cells are washed and the transduction may be repeated. After 16 hours, T-cells are washed and propagated in supplemented X-VIVO 20 media without rapamycin or IFN-α. On day 6, beads are removed; T-cells are then cryopreserved or expanded.

Each publication, patent, and patent publication cited in this disclosure is incorporated in reference herein in its entirety. The present invention is not intended to be limited to the foregoing examples but encompasses all such modifications and variations as come within the scope of the appended claims.

SEQUENCE LISTING

A Sequence Listing accompanies this application and is submitted as a ASCII text file of the sequence listing named "650053.00651_ST25.txt" which is 19.8 kb in size and was created on Nov. 26, 2019. The sequence listing is electronically submitted via EFS-Web with the application and is incorporated herein by reference in its entirety.

SEQUENCES:

SEQ ID NO: 1 CD19 CAR DNA SEQUENCE
ATGGCCTTACCAGTGACCGCCTTGCTCCTGCCGCTGGCCTTGCTGCTCCACGCCGCCAGG
CCGGAGGTGAAACTGCAGGAGTCAGGACCTGGCCTGGTGGCGCCCTCACAGAGCCTGTC
CGTCACATGCACTGTCTCAGGGGTCTCATTACCCGACTATGGTGTAAGCTGGATTCGCCA
GCCTCCACGAAAGGGTCTGGAGTGGCTGGGAGTAATATGGGGTAGTGAAACCACATACT
ATAATTCAGCTCTCAAATCCAGACTGACCATCATCAAGGACAACTCCAAGAGCCAAGTTT
TCTTAAAAATGAACAGTCTGCAAACTGATGACACAGCCATTTACTACTGTGCCAAACATT

```
ATTACTACGGTGGTAGCTATGCTATGGACTACTGGGGCCAAGGAACCTCAGTCACCGTCT
CCTCAGGTGGCGGTGGCTCGGGCGGTGGTGGGTCGGGTGGCGGCGGATCTGACATCCAG
ATGACACAGACTACATCCTCCCTGTCTGCCTCTCTGGGAGACAGAGTCACCATCAGTTGC
AGGGCAAGTCAGGACATTAGTAAATATTTAAATTGGTATCAGCAGAAACCAGATGGAAC
TGTTAAACTCCTGATCTACCATACATCAAGATTACACTCAGGAGTCCCATCAAGGTTCAG
TGGCAGTGGGTCTGGAACAGATTATTCTCTCACCATTAGCAACCTGGAGCAAGAAGATAT
TGCCACTTACTTTTGCCAACAGGGTAATACGCTTCCGTACACGTTCGGAGGGGGGACCAA
GCTGGAGATCACAACCACGACGCCAGCGCCGCGACCACCAACACCGGCGCCCACCATCG
CGTCGCAGCCCCTGTCCCTGCGCCCAGAGGCGTGCCGGCCAGCGGCGGGGGGCGCAGTG
CACACGAGGGGGCTGGACTTCGCCTGTGATATCTACATCTGGGCGCCCTTGGCCGGGACT
TGTGGGGTCCTTCTCCTGTCACTGGTTATCACCCTTTACTGCAAACGGGGCAGAAAGAAA
CTCCTGTATATATTCAAACAACCATTTATGAGACCAGTACAAACTACTCAAGAGGAAGAT
GGCTGTAGCTGCCGATTTCCAGAAGAAGAAGAAGGAGGATGTGAACTGAGAGTGAAGTT
CAGCAGGAGCGCAGACGCCCCCGCGTACAAGCAGGGCCAGAACCAGTCTCTATAACGAGC
TCAATCTAGGACGAAGAGAGGAGTACGATGTTTTGGACAAGACGTTGGCCGGGACCCT
GAGATGGGGGGAAAGCCGAGAAGGAAGAACCCTCAGGAAGGCCTGTACAATGAACTGC
AGAAAGATAAGATGGCGGAGGCCTACAGTGAGATTGGGATGAAAGGCGAGCGCCGGAG
GGGCAAGGGGCACGATGGCCTTTACCAGGGTCTCAGTACAGCCACCAAGGACACCTACG
ACGCCCTTCACATGCAGGCCCTGCCCCCTCGCTAG

SEQ ID NO: 2 CD19 CAR protein sequence
MALPVTALLLPLALLLHAARPEVKLQESGPGLVAPSQSLSVTCTV
SGVSLPDYGVSWIRQPPRKGLEWLGVIWGSETTYYNSALKSRLTII
KDNSKSQVFLKMNSLQTDDTAIYYAKHYYYGGSYAMDYWGQG
TSVTVSSGGGGSGGGGGSGGGGSDIQMTQTTSSLSASLGDRVTTSCR
ASQDISKYLNWYQQKPDGTVKLLIYHTSRLHSGVPSRFSGSGSGT
DYSLTISNLEQEDIATYFCQQGNTLPYTFGGGTKLEITTTTPAPRPP
TPAPTIASQPLSLRPEACRPAAGGAVHTRGLDFACDIYIWAPLAGT
CGVLLLSLVITLYCKRGRKKLLYIFKQPFMRPVQTTQEEDGCSCRF
PEEEEGGCELRVKFSRSADAPAYKQGQNQLYNELNLGRREEYDVL
DKRRGRDPEMGGKPRRKNPQEGLYNELQKDKMAEAYSEIGMKGE
RRRGKGHDGLYQGLSTATKDTYDALHMQALPPRStop SEQ ID NO: 3 Vector encoding CD19 CAR
PDY.CD19.CAR.HL.IRES.EGFP
GGGCGAATTGGGCCCGACGTCGCATGCTTGGAAGGGCTAATTCACTCCCAAAGAAGACA
AGATATCCTTGATCTGTGGATCTACCACACACAAGGCTACTTCCCTGATTAGCAGAACTA
CACACCAGGGCCAGGGGTCAGATATCCACTGACCTTTGGATGGTGCTACAAGCTAGTAC
CAGTTGAGCCAGATAAGGTAGAAGAGGCCAATAAAGGAGAGAACACCAGCTTGTTACAC
CCTGTGAGCCTGCATGGGATGGATGACCCGGAGAGAGAAGTGTTAGAGTGGAGGTTTGA
CAGCCGCCTAGCATTTCATCACGTGGCCCGAGAGCTGCATCCGGAGTACTTCAAGAACTG
CTGATATCGAGCTTGCTACAAGGGACTTTCCGCTGGGGACTTTCCAGGGAGGCGTGGCCT
GGGCGGGACTGGGGAGTGGCGAGCCCTCAGATCCTGCATATAAGCAGCTGCTTTTTGCCT
GTACTGGGTCTCTCTGGTTAGACCAGATCTGAGCCTGGGAGCTCTCTGGCTAACTAGGGA
ACCCACTGCTTAAGCCTCAATAAAGCTTGCCTTGAGTGCTTCAAGTAGTGTGTGCCCGTC
TGTTGTGTGACTCTGGTAACTAGAGATCCCTCAGACCCTTTTAGTCAGTGTGGAAAATCT
CTAGCAGTGGCGCCCGAACAGGGACTTGAAAGCGAAAGGGAAACCAGAGGAGCTCTCTC
GACGCAGGACTCGGCTTGCTGAAGCGCGCACGGCAAGAGGCGAGGGGCGGCGACTGGT
GAGTACGCCAAAAATTTTGACTAGCGGAGGCTAGAAGGAGAGAGATGGGTGCGAGAGC
GTCAGTATTAAGCGGGGAGAATTAGATCGCGATGGGAAAAAATTCGGTTAAGGCCAGG
GGGAAAGAAAAATATAAATTAAAACATATAGTATGGGCAAGCAGGGAGCTAGAACGA
TTCGCAGTTAATCCTGGCCTGTTAGAAACATCAGAAGGCTGTAGACAAATACTGGGACA
GCTACAACCATCCCTTCAGACAGGATCAGAAGAACTTAGATCATTATATAATACAGTAGC
AACCCTCTATTGTGTGCATCAAAGGATAGAGATAAAAGACACCAAGGAAGCTTTAGACA
AGATAGAGGAAGAGCAAAACAAAAGTAAGACCACCGCACAGCAAGCGGCCGCTGATCT
TCAGACCTGGAGGAGGAGATATGAGGGACAATTGGAGAAGTGAATTATATAAATATAAA
GTAGTAAAAATTGAACCATTAGGAGTAGCACCCACCAAGGCAAAGAGAAGAGTGGTGC
AGAGAGAAAAAAGAGCAGTGGGAATAGGAGCTTTGTTCCTTGGGTTCTTGGGAGCAGCA
GGAAGCACTATGGGCGCAGCGTCAATGACGCTGACGGTACAGGCCAGACAATTATTGTC
TGGTATAGTGCAGCAGCAGAACAATTTGCTGAGGGCTATTGAGGCGCAACAGCATCTGT
TGCAACTCACAGTCTGGGGCATCAAGCAGCTCCAGGCAAGAATCCTGGCTGTGGAAAGA
TACCTAAAGGATCAACAGCTCCTGGGGATTTGGGGTTGCTCTGGAAAACTCATTTGCACC
ACTGCTGTGCCTTGGAATGCTAGTTGGAGTAATAAATCTCTGGAACAGATTTGGAATCAC
ACGACCTGGATGGAGTGGGACAGAGAAATTAACAATTACACAAGCTTAATACACTCCTT
AATTGAAGAATCGCAAAACCAGCAAGAAAAGAATGAACAAGAATTATTGGAATTAGAT
AAATGGGCAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACTTTCTATAG
TGAATAGAGTTAGGCAGGGATATTCACCATTATCGTTTCAGACCCACCTCCCAACCCCGA
GGGGACCCGACAGGCCCGAAGGAATAGAAGAAGAAGGTGGAGAGAGAGACAGAGACA
GATCCATTCGATTAGTGAACGGATCTCGACGGGATCGATTTTAAAGAAAAGGGGGGAT
TGGGGGGTACAGTGCAGGGGAAAGAATAGTAGACATAATAGCAACAGACATACAAACT
AAAGAATTACAAAAACAAATTACAAAAATTCAAAATTTTATCGATAAGCTTTGCAAAGA
TGGATAAAGTTTTAAACAGAGAGGAATCTTTGCAGCTAATGGACCTTCTAGGTCTTGAAA
GGAGTGGGAATTGGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGGG
GTAAACTGGGAAAGTGATGTCGTGTACTGGCTCCGCCTTTTTCCCGAGGGTGGGGGAGA
ACCGTATATAAGTGCAGTAGTCGCCGTGAACGTTCTTTTTCGCAACGGGTTTGCCGCCAG
```

-continued

SEQUENCES:

```
AACACAGGTAAGTGCCGTGTGTGGTTCCCGCGGGCCTGGCCTCTTTACGGGTTATGGCCC
TTGCGTGCCTTGAATTACTTCCACCTGGCTGCAGTACGTGATTCTTGATCCCGAGCTTCGG
GTTGGAAGTGGGTGGGAGAGTTCGAGGCCTTGCGCTTAAGGAGCCCCTTCGCCTCGTGCT
TGAGTTGAGGCCTGGCCTGGGCGCTGGGGCCGCCGCGTGCGAATCTGGTGGCACCTTCGC
GCCTGTCTCGCTGCTTTCGATAAGTCTCTAGCCATTTAAAATTTTTGATGACCTGCTGCGA
CGCTTTTTTTCTGGCAAGATAGTCTTGTAAATGCGGGCCAAGATCTGCACACTGGTATTTC
GGTTTTTGGGGCCGCGGGCGGCGACGGGGCCCGTGCGTCCCAGCGCACATGTTCGGCGA
GGCGGGGCCTGCGAGCGCGGCCACCGAGAATCGGACGGGGGTAGTCTCAAGCTGGCCGG
CCTGCTCTGGTGCCTGGCCTCGCCGCCGTGTATCGCCCCGCCCTGGGCGGCAAGGCTG
GCCCGGTCGGCACCAGTTGCGTGAGCGGAAAGATGGCCGCTTCCCGGCCCTGCTGCAGG
GAGCTCAAAATGGAGGACGCGGCGCTCGGGAGAGCGGGCGGGTGAGTCACCCACACAA
AGGAAAAGGGCCTTTCCGTCCTCAGCCGTCGCTTCATGTGACTCCACGGAGTACCGGGCG
CCGTCCAGGCACCTCGATTAGTTCTCGAGCTTTTGGAGTACGTCGTCTTTAGGTTGGGGG
GAGGGGTTTTATGCGATGGAGTTTCCCCACACTGAGTGGGTGGAGACTGAAGTTAGGCC
AGCTTGGCACTTGATGTAATTCTCCTTGGAATTTGCCCTTTTTGAGTTTGGATCTTGGTTC
ATTCTCAAGCCTCAGACAGTGGTTCAAAGTTTTTTCTTCCATTTCAGGTGTCGTGAG
GAATTCCCCGGGAAGCCGCCACCATGGCCTTACCAGTGACCGCCTTGCTCCTGCCGCTGGCC
TTGCTGCTCCACGCCGCCAGGCCGGAGGTGAAACTGCAGGAGTCAGGACCTGGCCTGGTGGC
GCCCTCACAGAGCCTGTCCGTCACATGCACTGTCTCAGGGGTCTCATTACCCGACTATGGTG
TAAGCTGGATTCGCCAGCCTCCACGAAAGGGTCTGGAGTGGCTGGGAGTAATATGGGGTAGT
GAAACCACATACTATAATTCAGCTCTCAAATCCAGACTGACCATCATCAAGGACAACTCCAA
GAGCCAAGTTTTCTTAAAAATGAACAGTCTGCAAACTGATGACACAGCCATTTACTACTGTG
CCAAACATTATTACTACGGTGGTAGCTATGCTATGGACTACTGGGGCCAAGGAACCTCAGTC
ACCGTCTCCTCAGGTGGCGGTGGCTCGGGCGGTGGTGGGTCGGGTGGCGGCGGATCTGACAT
CCAGATGACACAGACTACATCCTCCCTGTCTGCCTCTCTGGGAGACAGAGTCACCATCAGTT
GCAGGGCAAGTCAGGACATTAGTAAATATTTAAATTGGTATCAGCAGAAACCAGATGGAACT
GTTAAACTCCTGATCTACCATACATCAAGATTACACTCAGGAGTCCCATCAAGGTTCAGTGG
CAGTGGGTCTGGAACAGATTATTCTCTCACCATTAGCAACCTGGAGCAAGAGATATTGCCA
CTTACTTTTGCCAACAGGGTAATACGCTTCCGTACACGTTCGGAGGGGGGACCAAGCTGGAG
ATCACAACCACGACGCCAGCGCCGCGACCACCAACACCGGCGCCCACCATCGCGTCGCAGCC
CCTGTCCCTGCGCCCAGAGGCGTGCCGGCCAGCGGCGGGGGGCGCAGTGCACACGAGGGGGC
TGGACTTCGCCTGTGATATCTACATCTGGGCGCCCTTGGCCGGGACTTGTGGGGTCCTTCTC
CTGTCACTGGTTATCACCCCTTTACTGCAAACGGGGCAGAAAGAAACTCCTGTATATATTCAA
ACAACCATTTATGAGACCAGTACAAACTACTCAAGAGGAAGATGGCTGTAGCTGCCGATTTC
CAGAAGAAGAAGAAGGAGGATGTGAACTGAGAGTGAAGTTCAGCAGGAGCGCAGACGCCCCC
GCGTACAAGCAGGGCCAGAACCAGCTCTATAACGAGCTCAATCTAGGACGAAGAGAGGAGTA
CGATGTTTTGGACAAGAGACGTGGCCGGGACCCTGAGATGGGGGGAAAGCCGAGAAGGAAGA
ACCCTCAGGAAGGCCTGTACAATGAACTGCAGAAAGATAAGATGGCGGAGGCCTACAGTGAG
ATTGGGATGAAAGGCGAGCGCCGGAGGGGCAAGGGGCACGATGGCCTTTACCAGGGTCTCAG
TACAGCCACCAAGGACACCTACGACGCCCTTCACATGCAGGCCCTGCCCCCTCGCTAGGGAT
CC
GCCCCTCTCCCTCCCCCCCCCCTAACGTTACTGGCCGAAGCCGCTTGGAATAAGGCCGGTGT
GCGTTTGTCTATATGTTATTTTCCACCATATTGCCGTCTTTTGGCAATGTGAGGGCCCGGAA
ACCTGGCCCTGTCTTCTTGACGAGCATTCCTAGGGGTCTTTCCCCTCTCGCCAAAGGAATGC
AAGGTCTGTTGAATGTCGTGAAGGAAGCAGTTCCTCTGGAAGCTTCTTGAAGACAAACAACG
TCTGTAGCGACCCTTTGCAGGCAGCGGAACCCCCCACCTGGCGACAGGTGCCTCTGCGGCCA
AAAGCCACGTGTATAAGATACACCTGCAAAGGCGGCACAACCCCAGTGCCACGTTGTGAGTT
GGATAGTTGTGGAAAGAGTCAAATGGCTCTCCTCAAGCGTATTCAACAAGGGGCTGAAGGAT
GCCCAGAAGGTACCCCATTGTATGGGATCTGATCTGGGGCCTCGGTACACATGCTTTACATG
TGTTTAGTCGAGGTTAAAAAAAACGTCTAGGCCCCCCGAACCACGGGGACGTGGTTTTCCTTT
GAAAAACACGATGTATATCATATGGCCACAACCATGGTGAGCAAGGGCGAGGAGCTGTTCACC
GGGGTGGTGCCCATCCTGGTCGAGCTGGACGGCGACGTAAACGGCCACAAGTTCAGCGTGTC
CGGCGAGGGCGAGGGCGATGCCACCTACGGCAAGCTGACCCTGAAGTTCATCTGCACCACCG
GCAAGCTGCCCGTGCCCTGGCCCACCCTCGTGACCACCCTGACCTACGGCGTGCAGTGCTTC
AGCCGCTACCCCGACCACATGAAGCAGCACGACTTCTTCAAGTCCGCCATGCCCGAAGGCTA
CGTCCAGGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTG
CCCGACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGAGCTGT
ACAAGTAAAGCGGCCGCGACTCAGATCCAAGCTTCAATTGTGGTCACTCGACAATCAACCTC
TGGATTACAAAATTTGTGAAAGATTGACTGGTATTCTTAACTATGTTGCTCCTTTTACGCTA
TGTGGATACGCTGCTTTAATGCCTTTGTATCATGCTATTGCTTCCCGTATGGCTTTCATTTT
CTCCTCCTTGTATAAATCTGGTTGCTGTCTCTTTATGAGGAGTTGTGGCCCGTTGTCAGGC
AACGTGGCGTGGTGTGCACTGTGTTTGCTGACGCAACCCCCACTGGTTGGGGCATTGCCACC
ACCTGTCAGCTCCTTTCCGGGACTTTCGCTTTCCCCCTCCCTATTGCCACGCGCGGAACTCAT
CGCCGCCTGCCTTGCCCGCTGCTGGACAGGGGCTCGGCTGTTGGGCACTGACAATTCCGTGG
TGTTGTCGGGGAAGCTGACGTCCTTTCCATGGCTGCTCGCCTGTGTTGCCACCTGGATTCTG
CGCGGGACGTCCTTCTGCTACGTCCCTTCGGCCCTCAATCCAGCGGACCTTCCTTCCCGCGG
CCTGCTGCCGGCTCTGCGGCCTCTTCCGCGTCTTCGCCTTCGCCCTCAGACGAGTCGGATCT
CCCTTTGGGCCGCCTCCCCGCCTGCTCGAGACCTAGAAAACATGGAGCAATCACAAGTAGC
AATACAGCAGCTACCAATGCTGATTGTGCCTGGCTAGAAGCACAAGAGGAGGAGGAGGTGGG
TTTTCCAGTCACACCTCAGGTACCTTTAAGACCAATGACTTACAAGGCAGCTGTAGATCTTA
GCCACTTTTTAAAAGAAAAGGGGGGACTGGAAGGGCTAATTCACTCCCAACGAAGACAAGAT
CTGCTTTTTGCTTGTACTGGGTCTCTCTGGTTAGACCAGATCTGAGCCTGGGAGCTCTCTGG
```

-continued

SEQUENCES:

```
CTAACTAGGGAACCCACTGCTTAAGCCTCAATAAAGCTTGCCTTGAGTGCTTCAAGTAGTGT
GTGCCCGTCTGTTGTGTGACTCTGGTAACTAGAGATCCCTCAGACCCTTTTAGTCAGTGTGG
AAAATCTCTAGCAGTAGTAGTTCATGTCATCTTATTATTCAGTATTTATAACTTGCAAAGAA
ATGAATATCAGAGAGTGAGAGGACGCGTTGGATGCATAGCTTGAGTATTCTATAGTGTCACC
TAAATAGCTTGGCGTAATCATGGTCATAGCTGTTTCCTGTGTGAAATTGTTATCCGCTCACA
ATTCCACACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAG
TACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATA
TTTGAATGTATTTAGAAAAATAAACAAATAGGGGTTCCGCGCACATTTCCCCGAAAAGTGCC
ACCTGATGCGGTGTGAAATACCGCACAGATGCGTAAGGAGAAAATACCGCATCAGGAAATTG
TAAGCGTTAATATTTTGTTAAAATTCGCGTTAAATTTTTGTTAAATCAGCTCATTTTTTAAC
CAATAGGCCGAAATCGGCAAAATCCCTTATAAATCAAAAGAATAGACCGAGATAGGGTTGAG
TGTTGTTCCAGTTTGGAACAAGAGTCCACTATTAAAGAACGTGGACTCCAACGTCAAAGGGC
GAAAAACCGTCTATCAGGGCGATGGCCCACTACGTGAACCATCACCCTAATCAAGTTTTTTG
GGGTCGAGGTGCCGTAAAGCACTAAATCGGAACCCTAAAGGGAGCCCCCGATTTAGAGCTTG
ACGGGGAAAGCCGGCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGCCGCGCTTAATGCG
CCGCTACAGGGCGCGTCCATTCGCCATTCAGGCTGCGCAACTGTTGGGAAGGGCGATCGGTG
CGGGCCTCTTCGCTATTACGCCAGCTGGCGAAAGGGGGATGTGCTGCAAGGCGATTAAGTTG
GGTAACGCCAGGGTTTTCCCAGTCACGACGTTGTAAAACGACGGCCAGTGAATTGTAATACG
ACTCACTATA
```

The invention claimed is:

1. A method of making a T-*Rapa* cell expressing a chimeric antigen receptor (CAR) comprising the steps of:
   (a) conditioning ex vivo CD3+T-cells with rapamycin to generate T-cells resistant to rapamycin (T-*Rapa* cells); and
   (b) transducing the T-*Rapa* cells in vitro with a vector that expresses the CAR to produce CAR-T-*Rapa* cells.

2. A CAR-T-*Rapa* cell comprising:
   an exogenous vector encoding and capable of expressing a chimeric antigen receptor (CAR), wherein the T-*Rapa* cells are made by culturing ex vivo CD3+T-cells in chemically defined medium comprising rapamycin for sufficient time to generate T-cells resistant to rapamycin (T-*Rapa* cells).

3. The CAR-T-*Rapa* cell of claim 2, wherein the T cells are obtained from a subject or suitable donor.

4. The CAR T-*Rapa* cell of claim 2, wherein the vector is a viral vector.

5. The CAR T-*Rapa* cell of claim 2, wherein the T cells are obtained from the subject or suitable donor by
   (i) obtaining a sample from the subject; and
   (ii) detecting and isolating CD3+T-cells from the sample and culturing the isolated T-cells in vitro.

6. The CAR T-*Rapa* cell of claim 2, wherein the vector is a lentiviral vector.

7. The CAR T-*Rapa* cell of claim 2, wherein the chemically defined medium comprises about 0.1 to about 2 micromolar rampamycin.

8. The CAR T-*Rapa* cells of claim 7, wherein the chemically defined medium comprises IL-2 and IFN-α.

9. The CAR T-*Rapa* cell of claim 2, wherein the CAR is a CAR specific to a tumor antigen.

10. The CAR T-*Rapa* cell of claim 2, wherein the CAR is a CD19 CAR.

11. A method of treating a subject diagnosed with a disease that is treatable with CAR therapy, the method comprising:
   administering an effective amount of the CAR-T-*Rapa* cell of claim 2 to treat the subject.

12. The method of claim 11, wherein the disease is cancer.

13. The method of claim 12, wherein the cancer is a hematologic cancer.

14. The method of claim 12, wherein the cancer is a solid tumor.

15. The method of claim 11, wherein the CAR-T-*Rapa* cells are introduced by intravenous transfusion.

16. A population comprising the CAR T-*Rapa* cells of claim 2, wherein at least 95% of the T *Rapa* cells express one or more biomarkers indicative of CAR expression.

17. The population of claim 16, wherein the population is capable of maintaining and expanding in_in vitro culture.

18. A stored population of CAR T *Rapa* cells, comprising the population of claim 17, a storage solution, and wherein the population is stored at or below about −80° C. in suitable storage solution until used.

19. A CAR-T-*Rapa* cell comprising:
   an exogenous vector encoding and capable of expressing a chimeric antigen receptor (CAR), wherein the CAR-T-*Rapa* cell is resistant to rapamycin.

* * * * *

UNITED STATES PATENT AND TRADEMARK OFFICE
CERTIFICATE OF CORRECTION

PATENT NO. : 12,076,344 B2
APPLICATION NO. : 17/296859
DATED : September 3, 2024
INVENTOR(S) : Jeffrey A. Medin et al.

It is certified that error appears in the above-identified patent and that said Letters Patent is hereby corrected as shown below:

In the Specification

Column 2, Line 52, "R54(11)" should be --RS4(11)--.

Column 2, Line 59, "CART" should be --CAR T--.

Column 2, Line 65, "literatures" should be --literature$^5$--.

Column 3, Line 4, "CART" should be --CAR T--.

Column 3, Line 12, "R54(11)" should be --RS4(11)--.

Column 11, Line 30, "ng/ml" should be --µg/ml--.

Signed and Sealed this
Fifth Day of November, 2024

Katherine Kelly Vidal
*Director of the United States Patent and Trademark Office*